US009138505B2

(12) United States Patent
Nogi et al.

(10) Patent No.: US 9,138,505 B2
(45) Date of Patent: Sep. 22, 2015

(54) POLYACRYLIC ACID (SALT)-TYPE WATER ABSORBENT RESIN AND METHOD FOR PRODUCING OF SAME

(75) Inventors: Kozo Nogi, Hyogo (JP); Kunihiko Ishizaki, Hyogo (JP); Katsuyuki Wada, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 575 days.

(21) Appl. No.: 13/392,256

(22) PCT Filed: Aug. 27, 2010

(86) PCT No.: PCT/JP2010/064641
§ 371 (c)(1),
(2), (4) Date: Feb. 24, 2012

(87) PCT Pub. No.: WO2011/024971
PCT Pub. Date: Mar. 3, 2011

(65) Prior Publication Data
US 2012/0172536 A1 Jul. 5, 2012

(30) Foreign Application Priority Data

| Aug. 27, 2009 | (JP) | 2009-196967 |
| Aug. 27, 2009 | (JP) | 2009-197022 |
| Aug. 27, 2009 | (JP) | 2009-197063 |
| Aug. 27, 2009 | (JP) | 2009-197091 |

(51) Int. Cl.
| C08F 20/02 | (2006.01) |
| A61L 15/24 | (2006.01) |
| C08J 3/24 | (2006.01) |
| A61L 15/60 | (2006.01) |
| C08F 120/06 | (2006.01) |
| C08F 220/06 | (2006.01) |

(52) U.S. Cl.
CPC ............... *A61L 15/24* (2013.01); *A61L 15/60* (2013.01); *C08F 120/06* (2013.01); *C08F 220/06* (2013.01); *C08J 3/24* (2013.01); *C08J 3/245* (2013.01); *C08J 2300/14* (2013.01); *C08J 2333/02* (2013.01)

(58) Field of Classification Search
USPC ............................ 525/329.7, 418, 119, 329.5
See application file for complete search history.

(56) References Cited

U.S. PATENT DOCUMENTS

| 4,734,478 A | 3/1988 | Tsubakimoto et al. |
| 4,755,562 A | 7/1988 | Alexander et al. |
| 4,783,510 A | 11/1988 | Saotome |
| 4,824,901 A | 4/1989 | Alexander et al. |
| 4,893,999 A | 1/1990 | Chmelir et al. |
| 5,124,416 A | 6/1992 | Haruna et al. |
| 5,140,076 A | 8/1992 | Hatsuda et al. |
| 5,206,205 A | 4/1993 | Tsai |
| 5,250,640 A | 10/1993 | Irie et al. |
| 5,409,771 A | 4/1995 | Dahmen et al. |
| 5,422,405 A | 6/1995 | Dairoku et al. |
| 5,610,208 A | 3/1997 | Dairoku et al. |
| 5,669,894 A | 9/1997 | Goldman et al. |
| 5,672,633 A | 9/1997 | Brehm et al. |
| 6,071,976 A | 6/2000 | Dairoku et al. |
| 6,228,930 B1 | 5/2001 | Dairoku et al. |
| 6,239,230 B1 | 5/2001 | Eckert et al. |
| 6,241,928 B1 | 6/2001 | Hatsuda et al. |
| 6,254,990 B1 | 7/2001 | Ishizaki et al. |
| 6,265,488 B1 | 7/2001 | Fujino et al. |

(Continued)

FOREIGN PATENT DOCUMENTS

| CN | 1530384 | 9/2004 |
| EP | 0349240 | 1/1990 |

(Continued)

OTHER PUBLICATIONS

Extended European Search Report dated Jan. 23, 2014 in EP 10812023.9.
Chinese Office Action dated Feb. 14, 2014 in CN 201080038386.5, and English translation thereof.
Office Action dated Jan. 7, 2014 in U.S. Appl. No. 13/392,240.
Notice of Reasons for Rejection dated Jun. 3, 2014 issued for Japanese Application No. 2011-528885 and its English Translation.

(Continued)

*Primary Examiner* — Monique Peets
(74) *Attorney, Agent, or Firm* — Roylance, Abrams, Berdo & Goodman, L.L.P.

(57) ABSTRACT

Disclosed is a method for producing a water absorbent resin, by which a surface-crosslinked water absorbent resin having excellent physical properties can be efficiently obtained at low cost, while assuring high productivity. When the production scale is increased to a continuous production on a huge scale (for example, 1 t/hr or more), the physical properties are improved and stabilized (for example, standard deviation of the physical properties is reduced) by a surface-crosslinking treatment, and the absorption against pressure (AAP) and liquid permeability (SFC) are further improved. Specifically disclosed is a method for continuously producing a polyacrylic acid (salt)-type water absorbent resin powder, which comprises: a step of preparing an aqueous monomer solution using an acrylic acid (salt); a step of polymerizing the aqueous monomer solution; a shredding step of a hydrous gel-like crosslinked polymer during or after the polymerization; a step of drying the thus-obtained particulate hydrous gel-like crosslinked polymer; a step of crushing and classifying the dried product; a step of heating and surface-crosslinking after the classification; and a step of cooling after the surface-crosslinking. In the method for producing a polyacrylic acid (salt)-type water absorbent resin, the internal area of the cooling device that is used in the cooling step is 0.25-0.95 times the internal area of the heating device that is used in the surface-crosslinking step.

16 Claims, 2 Drawing Sheets

(56) References Cited

U.S. PATENT DOCUMENTS

| | | |
|---|---|---|
| 6,297,319 B1 | 10/2001 | Nagasuna et al. |
| 6,300,423 B1 | 10/2001 | Engelhardt et al. |
| 6,372,852 B2 | 4/2002 | Hitomi et al. |
| 6,472,478 B1 | 10/2002 | Funk et al. |
| 6,503,979 B1 | 1/2003 | Funk et al. |
| 6,514,615 B1 | 2/2003 | Sun et al. |
| 6,559,239 B1 | 5/2003 | Riegel et al. |
| 6,576,713 B2 | 6/2003 | Ishizaki et al. |
| 6,605,673 B1 | 8/2003 | Mertens et al. |
| 6,620,889 B1 | 9/2003 | Mertens et al. |
| 6,620,899 B1 | 9/2003 | Morken et al. |
| 6,657,015 B1 | 12/2003 | Riegel et al. |
| 6,710,141 B1 | 3/2004 | Heide et al. |
| 6,720,389 B2 | 4/2004 | Hatsuda et al. |
| 6,809,158 B2 | 10/2004 | Ikeuchi et al. |
| 6,906,159 B2 | 6/2005 | Dairoku et al. |
| 6,987,151 B2 | 1/2006 | Gartner et al. |
| 7,091,253 B2 | 8/2006 | Dairoku et al. |
| 7,098,284 B2 | 8/2006 | Torii et al. |
| 7,157,141 B2 | 1/2007 | Inger et al. |
| 7,183,456 B2 | 2/2007 | Hatsuda et al. |
| 7,312,278 B2 | 12/2007 | Nakashima et al. |
| 7,378,453 B2 | 5/2008 | Nogi et al. |
| 7,473,739 B2 | 1/2009 | Dairoku et al. |
| 7,528,291 B2 | 5/2009 | Herfert |
| 7,541,395 B2 | 6/2009 | Reimann et al. |
| 7,803,880 B2 * | 9/2010 | Torii et al. .................. 525/329.7 |
| 7,833,624 B2 | 11/2010 | Harren et al. |
| 7,851,550 B2 | 12/2010 | Kadonaga et al. |
| 7,893,134 B2 | 2/2011 | Reimann et al. |
| 7,910,675 B2 | 3/2011 | Funk et al. |
| 8,071,202 B2 | 12/2011 | Furno et al. |
| 2001/0025093 A1 | 9/2001 | Ishizaki et al. |
| 2003/0020199 A1 | 1/2003 | Kajikawa et al. |
| 2004/0106745 A1 | 6/2004 | Nakashima et al. |
| 2004/0110913 A1 | 6/2004 | Kanto et al. |
| 2004/0181031 A1 | 9/2004 | Nogi et al. |
| 2004/0240316 A1 | 12/2004 | Nogi et al. |
| 2005/0029352 A1 | 2/2005 | Spears |
| 2005/0048221 A1 | 3/2005 | Irie et al. |
| 2005/0051925 A1 | 3/2005 | Gartner et al. |
| 2005/0070671 A1 | 3/2005 | Torii et al. |
| 2005/0215734 A1 | 9/2005 | Dairoku et al. |
| 2005/0288182 A1 | 12/2005 | Torii et al. |
| 2006/0029782 A1 | 2/2006 | Harren et al. |
| 2006/0057389 A1 | 3/2006 | Reimann et al. |
| 2006/0073969 A1 | 4/2006 | Torii et al. |
| 2006/0252913 A1 | 11/2006 | Herfert |
| 2006/0276598 A1 | 12/2006 | Wada et al. |
| 2007/0078231 A1 | 4/2007 | Shibata et al. |
| 2007/0106013 A1 | 5/2007 | Adachi et al. |
| 2007/0123658 A1 | 5/2007 | Torii et al. |
| 2007/0149760 A1 | 6/2007 | Kadonaga et al. |
| 2007/0161759 A1 | 7/2007 | Riegel et al. |
| 2007/0293632 A1 | 12/2007 | Riegel et al. |
| 2008/0221277 A1 | 9/2008 | Walden et al. |
| 2008/0227932 A1 | 9/2008 | Funk et al. |
| 2008/0280128 A1 | 11/2008 | Furno et al. |
| 2009/0105389 A1 | 4/2009 | Walden et al. |
| 2009/0202805 A1 | 8/2009 | Furno et al. |
| 2009/0209683 A1 | 8/2009 | Reimann et al. |
| 2009/0227741 A1 | 9/2009 | Walden et al. |
| 2009/0314258 A1 | 12/2009 | Azou |
| 2010/0072421 A1 | 3/2010 | Kitano et al. |
| 2010/0140546 A1 | 6/2010 | Barthel et al. |
| 2010/0249320 A1 | 9/2010 | Matsumoto et al. |
| 2011/0003926 A1 | 1/2011 | Nogi et al. |
| 2011/0006140 A1 | 1/2011 | Ishizaki et al. |
| 2011/0009590 A1 | 1/2011 | Matsumoto et al. |
| 2011/0011491 A1 | 1/2011 | Matsumoto et al. |
| 2011/0015351 A1 | 1/2011 | Nogi et al. |
| 2011/0028670 A1 | 2/2011 | Matsumoto et al. |
| 2011/0088806 A1 | 4/2011 | Nogi et al. |
| 2011/0110730 A1 | 5/2011 | Nogi et al. |
| 2011/0166300 A1 | 7/2011 | Dairoku et al. |

FOREIGN PATENT DOCUMENTS

| | | |
|---|---|---|
| EP | 0534228 | 3/1993 |
| EP | 0603292 | 6/1994 |
| EP | 1824910 | 8/2007 |
| JP | 54-010387 | 1/1979 |
| JP | 2-049002 | 2/1990 |
| JP | 3-168218 | 7/1991 |
| JP | 5-112654 | 5/1993 |
| JP | 5-202199 | 8/1993 |
| JP | 2000-143720 | 5/2000 |
| JP | 2002-121291 | 4/2002 |
| JP | 2004-300425 | 10/2004 |
| JP | 2004-345804 | 12/2004 |
| JP | 2004-352941 | 12/2004 |
| JP | 2004-359943 | 12/2004 |
| JP | 2006-503949 | 2/2006 |
| JP | 2006522181 A | 9/2006 |
| JP | 2008-038128 | 2/2008 |
| JP | 2008-255366 | 10/2008 |
| JP | 2009-506151 | 2/2009 |
| JP | 2009-518484 | 5/2009 |
| WO | 2004/069915 | 8/2004 |
| WO | 2005/016393 | 2/2005 |
| WO | 2006/082188 | 8/2006 |
| WO | 2006/082189 | 8/2006 |
| WO | 2006/082197 | 8/2006 |
| WO | 2006/109842 | 10/2006 |
| WO | 2006/111402 | 10/2006 |
| WO | 2006/111403 | 10/2006 |
| WO | 2006/111404 | 10/2006 |
| WO | 2007/065840 | 6/2007 |
| WO | 2007/121037 | 10/2007 |
| WO | 2008/009842 | 1/2008 |
| WO | 2008/009843 | 1/2008 |
| WO | 2008/108277 | 9/2008 |
| WO | 2009/001954 | 12/2008 |
| WO | 2009/028568 | 3/2009 |
| WO | 2009/113672 | 9/2009 |
| WO | 2009/113673 | 9/2009 |
| WO | 2009/113679 | 9/2009 |

OTHER PUBLICATIONS

Notice of Reasons for Rejection dated Jun. 24, 2014 issued for Japanese Application No. 2011-528882 and its English Translation.
Office Action, dated Jul. 22, 2014, in U.S. Appl. No. 13/392,240.
Chinese Office Action, dated Sep. 17, 2013, in related CN Appln. No. 201080038364.9, and its English translation.
Chinese Office Action, dated Aug. 29, 2013, in related CN Appln. No. 201080038386.5, and its English translation.
Chinese Office Action, dated Jan. 15, 2013, in related CN Appln. No. 201080038386.5, and its English translation.
Chinese Office Action, dated Jan. 15, 2013, in related CN Appln. No. 201080038364.9, and its English translation.
International Search Report for PCT/JP2010/064641, dated Sep. 28, 2010.
Office Action dated Nov. 20, 2013 in U.S. Appl. No. 13/392,639.
Office Action dated Dec. 23, 2013 in U.S. Appl. No. 13/392,214.
Supplementary Partial European Search Report, dated Jan. 15, 2015, in EP Application No. 10812024.7.
Supplementary European Search Report, dated Jan. 28, 2015, in EP Application No. 10812020.5.
Extended European Search Report, dated Dec. 16, 2014, in related EP Application No. 10812021.3.
Advisory Action, dated Oct. 27, 2014, issued in U.S. Appl. No. 13/392,240.
Extended European Search Report, dated Jun. 10, 2015, in EP Application No. 10812024.7.

* cited by examiner

POLYACRYLIC ACID (SALT)-TYPE WATER ABSORBENT RESIN AND METHOD FOR PRODUCING OF SAME

TECHNICAL FIELD

The present invention relates to a polyacrylic acid (salt)-type water absorbent resin and a method for producing the same. More particularly, the present invention relates to a polyacrylic acid (salt)-type water absorbent resin having high water absorption rate (CRC), high water absorption against pressure (AAP), and high liquid permeability (SFC) and containing little water extractables and a method for producing the same.

BACKGROUND ART

A water absorbent resin (Super Absorbent Polymer; abbreviated as SAP) has been used in a wide range of uses for sanitary materials such as paper diapers, sanitary napkins, incontinence products for adults, and the like, and uses for water retention agent for soil, owing to properties that the resin can absorb a large quantity of a water-based liquid several times to several hundred times as much as the mass of itself and has been manufactured and consumed in large quantities.

In general, a water absorbent resin is produced by polymerizing an aqueous solution containing a hydrophilic monomer and a crosslinking agent to obtain a hydrous gel-like polymer, drying the gel polymer, and surface-crosslinking the dried product. The physical properties such as water absorption against pressure (AAP) and liquid permeability (GBP, SFC) of the above-mentioned water absorbent resin are improved by surface-crosslinking step. The surface-crosslinking step is commonly a step of providing a highly crosslinked layer in the vicinity of the water absorbent resin surface by causing reaction of the water absorbent resin with a surface-crosslinking agent or a polymerizable monomer.

Various kinds of surface-crosslinking agents reactive on a functional group of a water absorbent resin (particularly, carboxyl group) are proposed as a surface-reforming method of such a water absorbent resin and examples known as the surface-crosslinking agents are oxazoline compounds (Patent Document 1), vinyl ether compounds (Patent Document 2), epoxy compounds (Patent Document 3), oxetane compounds (Patent Document 4), polyhydric alcohol compounds (Patent Document 5), polyamide polyamine-epihalo adducts (Patent Documents 6, 7), hydroxyacrylamide compounds (Patent Document 8), oxazolidinone compounds (Patent Documents 9, 10), bis- or poly-oxazoline compounds (Patent Document 11), 2-oxotetrahydro-1,3-oxazolidine compounds (Patent Document 12), alkylene carbonate compounds (Patent Document 13), and the like. A technique using a specified surface-crosslinking agent (Patent Document 14) is also known.

Techniques also known as the surface-reforming method other than the method carried out by a surface-crosslinking agent are a technique of surface-crosslinking by polymerizing a monomer in the vicinity of the water absorbent resin surface (Patent Document 15) and techniques of radical crosslinking with persulfuric acid salts etc. (Patent Documents 16, 17). Techniques of reforming water absorbent resins by heating without using a surface-crosslinking agent (Patent Documents 18, 19), which is different from common surface-crosslinking treatment, are also known.

A technique of using an additive in combination for mixing a surface-crosslinking agent is also proposed and examples known as the additive are water-soluble cations such as aluminum salts and the like (Patent Documents 20, 21), alkali (Patent Document 22), organic acids or inorganic acids (Patent Document 23), peroxides (Patent Document 24), and surfactants (Patent Document 25).

Not only the chemical methods but also many surface treatment methods using apparatuses and reaction conditions have been proposed. Examples known as a method using an apparatus are techniques using a specified mixing apparatus as a mixing apparatus for a surface-crosslinking agent (Patent Documents 26 to 29) and techniques using a heating apparatus for causing reaction of a water absorbent resin and a surface-crosslinking agent (Patent Documents 30, 31) and the like.

There is also a technique for controlling an increase in heating temperature for causing reaction of a water absorbent resin and a surface-crosslinking agent (Patent Document 32) in improvement of the reaction condition aspect. In a heating step, techniques known are a technique of carrying out surface-crosslinking twice (Patent Document 33), a technique of controlling particle size by drying a water absorbent resin, thereafter carrying out a second heat drying step, and further carrying out surface-crosslinking (Patent Document 34), a technique of defining oxygen partial pressure (Patent Document 35), techniques of defining the spraying conditions and dew points (Patent Documents 37, 38), techniques of defining the mixing conditions of treatment liquids (Patent Documents 39, 40), and a technique paying attention to a cooling step (Patent Document 41).

PRIOR ART DOCUMENTS

Patent Documents

Patent Document 1: U.S. Pat. No. 6,297,319
Patent Document 2: U.S. Pat. No. 6,372,852
Patent Document 3: U.S. Pat. No. 6,265,488
Patent Document 4: U.S. Pat. No. 6,809,158
Patent Document 5: U.S. Pat. No. 4,734,478
Patent Document 6: U.S. Pat. No. 4,755,562
Patent Document 7: U.S. Pat. No. 4,824,901
Patent Document 8: U.S. Pat. No. 6,239,230
Patent Document 9: U.S. Pat. No. 6,559,239
Patent Document 10: U.S. Pat. No. 6,503,979
Patent Document 11: U.S. Pat. No. 6,472,478
Patent Document 12: U.S. Pat. No. 6,657,015
Patent Document 13: U.S. Pat. No. 5,409,771
Patent Document 14: U.S. Pat. No. 5,422,405
Patent Document 15: US Patent Application Publication No. 2005/048221
Patent Document 16: U.S. Pat. No. 4,783,510
Patent Document 17: EP Patent No. 1824910
Patent Document 18: U.S. Pat. No. 5,206,205
Patent Document 19: EP Patent No. 0603292
Patent Document 20: U.S. Pat. No. 6,605,673
Patent Document 21: U.S. Pat. No. 6,620,899
Patent Document 22: U.S. Pat. No. 7,312,278
Patent Document 23: U.S. Pat. No. 5,610,208
Patent Document 24: US Patent Application Publication No. 2007/078231
Patent Document 25: US Patent Application Publication No. 2005/029352
Patent Document 26: U.S. Pat. No. 5,140,076
Patent Document 27: U.S. Pat. No. 6,071,976
Patent Document 28: US Patent Application Publication No. 2004/240316
Patent Document 29: WO No. 2007/065840 pamphlet Patent Document 30: US Patent Application Publication No. 2007/149760

Patent Document 31: Japan Patent Application Publication No. 2004-352941

Patent Document 32: U.S. Pat. No. 6,514,615

Patent Document 33: U.S. Pat. No. 5,672,633

Patent Document 34: WO No. 2009/028568 pamphlet

Patent Document 35: US Patent Application Publication No. 2007/0293632

Patent Document 36: U.S. Pat. No. 6,720,389

Patent Document 37: U.S. Pat. No. 7,183,456

Patent Document 38: US Patent Application Publication No. 2007/161759

Patent Document 39: US Patent Application Publication No. 2006/057389

Patent Document 40: EP Patent No. 0534228

Patent Document 41: U.S. Pat. No. 7,378,453

DISCLOSURE OF THE INVENTION

Problems to be Solved by the Invention

It is difficult to satisfy demands from users for physical properties such as water absorption against pressure and liquid permeability of a water absorbent resin only by a surface-crosslinking technique, although there have been proposed many of surface-crosslinking agents (see Patent Documents 1 to 13) and their combination use (see Patent Document 14), auxiliary agents for surface-crosslinking (see Patent Documents 20 to 25), their mixing apparatuses (see Patent Documents 26 to 29) and heating apparatuses (Patent Documents 30, 31), and also various kinds of conditions (see Patent Documents 32 to 41). Along with change of a surface-crosslinking agent and use of a new auxiliary agent, it may be sometimes accompanied with an increase in cost, a decrease in safety, deterioration of other physical properties (e.g., coloration), and the like in some cases. Although causing an effect to a certain extent in a small scale or batch type production in an experimental laboratory level, the above-mentioned means may not sometimes show so much effective in an industrial scale (e.g., 1 t or more per unit hour) such as large scale continuous production as compared with that in a small scale.

For example, Patent Document 41 describes prevention of the dew formation of moisture generated along with the process of the surface-crosslinking reaction and production troubles and deterioration of resin physical properties due to consequent agglomeration of resin particles by stirring and cooling a water absorbent resin powder after heating treatment under air flow, in a method of carrying out surface-crosslinking treatment for the water absorbent resin particles by adding a surface-crosslinking agent thereto and carrying out heat treatment; however, it cannot be said that the effect is sufficiently exerted.

The present invention has been completed in terms of the problems, and an object of the present invention is to provide a method for producing a water absorbent resin which is excellent in physical properties and surface-crosslinked efficiently at a low cost while assuring high productivity.

Solutions to the Problems

The present inventors have made investigations on a surface-crosslinking step for solving the problems and consequently have solved the problems by carrying out the heat treatment with a specified apparatus in the surface treatment step after addition of a surface-crosslinking agent and at the same time carrying out the cooling step with a specified apparatus after the surface-crosslinking.

That is, to solve the above-mentioned problems, the present invention provide a continuous method for producing water absorbent resin powder (the first method), comprising steps of;

preparing an aqueous monomer solution of acrylic acid (salt), polymerizing the aqueous monomer solution, finely shredding a hydrous gel-like crosslinked polymer during or after polymerization, drying the obtained particulate hydrous gel-like crosslinked polymer, crushing the dried product, classifying the dried product, heating and surface-crosslinking the dried product after the classification, and cooling after the surface-crosslinking, wherein the inner surface area of a cooling apparatus to be used in the cooling step is 0.25 to 0.95 times as large as the inner surface area of a heating apparatus to be used in the heating and surface-crosslinking step.

That is, to solve the above-mentioned problems, the present invention provide a continuous method for producing water absorbent resin powder (the second method), comprising steps of:

preparing an aqueous monomer solution of acrylic acid (salt), polymerizing the aqueous monomer solution, finely shredding a hydrous gel-like crosslinked polymer during or after polymerization, drying the obtained particulate hydrous gel-like crosslinked polymer, crushing the dried product, classifying the dried product, heating and surface-crosslinking the dried product after the classification, and cooling after the surface-crosslinking, wherein the inner volume of a cooling apparatus to be used in the cooling step is 0.25 to 0.95 times as large as the inner volume of a heating apparatus to be used in the heating and surface-crosslinking step.

In addition, the first method and the second method are preferably employed in combination.

Effects of the Invention

According to the present invention, in continuous production in a large industrial scale (particularly, treatment amount of 1 t/hr or more), the physical properties (e.g., water absorption against pressure and liquid permeability) can be improved after surface-crosslinking and the fluctuation of physical property (standard deviation) can be narrowed.

MODE FOR CARRYING OUT THE INVENTION

Figure 1:
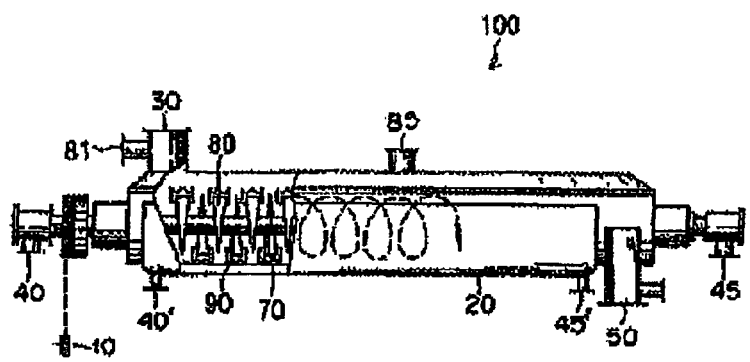
FIG. 1 is a cross-sectional view showing one example of the configuration of a heating apparatus or a cooling apparatus having a biaxial transverse type continuous stirring apparatus and being employed in the embodiment of the present invention.

Hereinafter, the polyacrylic acid (salt)-type water absorbent resin of the present invention and a method for producing the same will be described in detail; however, the scope of the present invention is not restricted to the following description, and those other than the following examples can be properly modified and carried out in a range where the gist of the present invention is not impaired. Specifically, the present invention is not limited to each of the following embodiments, and various modifications can be made within a range shown by the claims and embodiments carried out by properly combining each technical means disclosed with different embodiments are also included within the technical scope of the present invention.

[1] DEFINITION OF TERMS (a) "Water Absorbent Resin"

The "water absorbent resin" means water-swelling and water-insoluble "polymer gelling agent" and includes those having the following physical properties. That is, those having, as the water-swelling property, a water absorption rate under no pressure (CRC) of 5 g/g or more. CRC is preferably 10 to 100 g/g and more preferably 20 to 80 g/g. Because of water-insolubility, it is required that water extractables are in amount of 0 to 50 mass %. The water extractables are preferably in amount of 0 to 30 mass %, more preferably in amount of 0 to 20 mass %, and even preferably in amount of 0 to 10 mass %.

The water absorbent resin is not limited to be embodiments of 100 mass % of a polymer and may contain other additives (described below) to the extent of retaining the above-mentioned characteristics. That is, even a water absorbent resin composition having the water absorbent resin and additives is generally named as a water absorbent resin in the present invention. The content of the polyacrylic acid (salt)-type water absorbent resin is preferably 70 to 99.9 mass % relative to the entire water absorbent resin, more preferably 80 to 99.7 mass %, and still more preferably 90 to 99.5 mass %. The components other than the water absorbent resin are preferably water in terms of the water absorption speed and impact resistance of powder (particles) and may include, if necessary, additives described below.

(b) "Polyacrylic Acid (Salt)"

The "polyacrylic acid (salt)" means a polymer containing arbitrarily a graft component and, as a repeating unit, an acrylic acid (salt) as a main component. The acrylic acid (salt) as a monomer excluding a crosslinking agent is in an amount of essentially 50 to 100% by mole, preferably 70 to 100% by mole, more preferably 90 to 100% by mole, and still more preferably substantially 100% by mole. The acrylic acid salt as the polymer essentially contains a polyacrylic acid salt and preferably contains a monovalent salt, more preferably an alkali metal salt or ammonium salt, still more preferably an alkali metal salt, and particularly preferably sodium salt. The shape is not particularly limited; however, the polyacrylic acid (salt) is preferably particles or a powder.

(c) "EDANA" and "ERT"

"EDANA" is an abbreviation of European Disposables and Nonwovens Associations. "ERT" is an abbreviation of measurement method (ERT/EDANA Recommended Test Method) of a water absorbent resin on the basis of European Standards (almost Global Standards) as defined below. In this specification, unless otherwise specified, the physical properties of a water absorbent resin are measured based on ERT original text (Known Document: revised in 2002).

(c-1) CRC (ERT441.2-02)

The "CRC" is an abbreviation for Centrifuge Retention Capacity and means water absorption rate under no pressure (simply sometimes referred to as "water absorption rate"). Specifically, the CRC is the water absorption rate (unit; g/g) after 0.200 g of a water absorbent resin in a nonwoven fabric bag is freely swollen in 0.9 mass % saline solution for 30 minutes and dewatered by a centrifuge at 250 G.

(c-2) AAP (ERT442.2-02)

The "AAP" is an abbreviation for Absorption Against Pressure and means water absorption against pressure. Specifically, the APP is the water absorption rate (unit; g/g) after 0.900 g of a water absorbent resin is swollen in 0.9 mass % saline solution for 1 hour under 1.9 kPa load. In the present invention and examples, the measurement is carried out at 4.8 kPa.

(c-3) "Extractables" (ERT 470.2-02)

"Extractables" means the amount of water soluble components (dissolve amount). Specifically, measurement is carried out by adding 1.000 g of the water absorbent resin to 200 ml of an 0.9 mass % aqueous saline solution, stirring the solution for 16 hours, and measuring the amount of a dissolved polymer by pH titration (unit: mass %).

(c-4) Residual Monomers (ERT410.2-02)

The "residual monomers" means the amount of monomers remaining in a water absorbent resin. Specifically, the amount of monomers is a value (unit; ppm by mass) obtained by measuring, after 1.000 g of a water absorbent resin is charged to 200 $cm^3$ of 0.9 mass % saline solution and the resultant is stirred for 2 hours, the amount of monomers eluted in the aqueous solution by using high-pressure liquid chromatography.

(c-5) PSD (ERT420.2-02)

The "PSD" is an abbreviation for Particle Size Distribution and means the particle size distribution measured by sieving classification. The mass average particle diameter and the particle diameter distribution width can be measured by the same method as in "(1) Average Particle Diameter and Distribution of Particle Diameter" described in European Patent No. 0349240, p. 7, lines 25-43 and WO 2004/069915.

(c-6) Others

"pH" (ERT400.2-02): The "pH" means pH of a water absorbent resin.

"Moisture Content" (ERT 430.2-02): The moisture content means the water content of a water absorbent resin.

"Flow Rate" (ERT 450.2-02): The flow rate means the flow down speed of a water absorbent resin powder.

"Density" (ERT 460.2-02): The density means the bulk specific density of a water absorbent resin.

(d) "Liquid Permeability"

The "liquid permeability" means the flow of a liquid flowing among particles of swollen gel under a load or no load. The "liquid permeability" can be measured by SFC (Saline Flow Conductivity) or GBP (Gel Bed Permeability) as a representative measurement method.

The "SFC" is liquid permeability of 0.69 mass % physiological saline solution in a water absorbent resin at a load of 0.3 psi. It is measured according to an SFC testing method described in U.S. Pat. No. 5,669,894.

The "GBP" is liquid permeability of 0.69 mass % physiological saline solution in a water absorbent resin under a load or free expansion. It is measured according to a GBP testing method described in WO 2005/016393 pamphlet.

(e) "Standard Deviation"

The "standard deviation" is a numeral value showing the degree of dispersion of data and means a positive square root of the value calculated by totalizing the square value of the difference of the value of data of n samples and their arithmetic average, that is, the deviation, and dividing the total by n−1. It is used for understanding the degree of fluctuation for the phenomenon with considerable fluctuation. In this specification, the standard deviation is employed for digitalization of the fluctuation (deflection) for a desired physical value of interest.

[Numeral 1]

Data of $n$ samples $X1, X2, \ldots, Xn$

Arithmetic average $X = \frac{1}{n}\sum_{i=1}^{n} Xi$

Standard deviation $= \sqrt{\frac{1}{n-1}\sum_{i=1}^{n}(Xi-X)^2}$ (f) Others

In this specification, "X to Y" showing a range means "X or more and Y or lower". Additionally, the unit of mass "t (ton)" means "Metric ton". Further, the measurement of physical properties of a water absorbent resin is carried out under the conditions of a temperature of 20 to 25° C. (sometimes simply referred to as "room temperature" or "normal temperature") and a relative humidity of 40 to 50%, unless otherwise stated.

[2] A METHOD FOR PRODUCING POLYACRYLIC ACID (SALT)-TYPE WATER ABSORBENT RESIN (1) Polymerization Step (a) Monomer (Excluding a Crosslinking Agent)

A monomer of the present invention contains the above-mentioned acrylic acid or its salt as a main component and in terms of water absorption characteristics and decrease of the residual monomers, the acid groups of a polymer are preferable to be neutralized and the neutralization ratio is 10 to 100% by mole preferable, more preferably 30 to 95% by mole, still more preferably 50 to 90% by mole, and particularly preferably 60 to 80% by mole. The neutralization may be carried out for the polymer (hydrogel) after polymerization or for the monomer; however, in terms of productivity and improvement of AAP, neutralization of the monomer is preferable. Consequently, the monomer in the present invention includes a partially neutralized salt of the acrylic acid.

Further, in the present invention, a hydrophilic or hydrophobic unsaturated monomer may be used besides an acrylic acid (salt). Monomers usable may include methacrylic acid, maleic acid, maleic anhydride, 2-(meth)acrylamido-2-methylpropanesulfonic acid, (meth)acryloxyalkanesulfonic acid, N-vinyl-2-pyrrolidone, N-vinylacetamide, (meth)acrylamide, N-isopropyl(meth)acrylamide, N,N-dimethyl(meth) acrylamide, 2-hydroxyethyl(meth)acrylate, methoxypolyethylene glycol(meth)acrylate, polyethylene glycol(meth) acrylate, stearyl acrylate, and their salts.

(b) Crosslinking Agent (Inner Crosslinking Agent)

In the present invention, in terms of the water absorbent properties, use of a crosslinking agent (i.e.; inner crosslinking agent) is preferable. The crosslinking agent is used in an amount of preferably 0.001 to 5% by mole, more preferably 0.005 to 2% by mole, still more preferably 0.01 to 1% by mole, and particularly preferably 0.03 to 0.5% by mole to the monomer excluding the crosslinking agent, in terms of physical aspect.

Examples usable as the crosslinking agent are one or more of polymerizable crosslinking agents (with polymerizable double bond of the acrylic acid), reactive crosslinking agents (with a carboxyl group of the monomer), and crosslinking agents having both of these properties. Concrete examples are, as a polymerizable crosslinking agent, compounds having at least two polymerizable double bonds in a molecule such as N,N-methylenebisacrylamide, (poly)ethylene glycol di(meth)acrylate, (polyoxyethylene)trimethylolpropane tri (meth)acrylate, poly(meth)allyloxyalkanes etc. Further, examples of the reactive crosslinking agent are covalent-binding crosslinking agents such as polyglycidyl ether (ethylene glycol diglycidyl ether or the like), poly alcohols (propanediol, glycerin, sorbitol, etc.), and ion-binding crosslinking agents such as polyvalent metal compounds of aluminum or the like. Among these crosslinking agents, in terms of water absorbent properties, polymerizable crosslinking agents (with the acrylic acid), particularly, acrylate type, allyl type, and acrylamide type polymerizable crosslinking agents are preferably used.

(c) Neutralizing Salt

Preferable examples as a basic substance to be used for neutralization of the acrylic acid may include monovalent bases such as alkali metal hydroxides such as sodium hydroxide, potassium hydroxide, and lithium hydroxide etc., and alkali metal (hydrogen) carbonates such as sodium (hydrogen) carbonate, potassium (hydrogen) carbonate, etc. Particularly, in terms of decrease of the residual monomers, neutralization into an alkali metal acrylate especially with sodium hydroxide is preferable. The preferable conditions or the like in these neutralization treatments are exemplified in International Publication No. 2006/522181 and the disclosed conditions are applicable for the present invention. The neutralization temperature is preferably in a range of 10 to 100° C., more preferably in a range of 30 to 90° C.

The neutralization temperature is properly determined in this range, and a neutralization method described below is preferable to decrease the residual monomers.

(d) Concentration of Monomer

Monomers may be polymerized generally in an aqueous solution. The solid content is generally 10 to 90 mass %, preferably 20 to 80 mass %, more preferably 30 to 70 mass %, and particularly preferably 35 to 60 mass %. The polymerization may be carried out in the form of a slurry (water dispersion liquid) exceeding the saturated concentration; however, in terms of physical properties, it is carried out in an aqueous solution with the saturated concentration or lower.

(e) Other Monomer Components

The aqueous unsaturated monomer solution may contain a water-soluble resin or a water absorbent resin such as starch, polyacrylic acid (salt), or polyethylene imine, in combination with a monomer, in an amount of, for example, 0 to 50 mass %, preferably 0 to 20 mass %, particularly preferably 0 to 10 mass %, and most preferably 0 to 3 mass %. The solution may further contain a various kinds of foaming agents (carbonates, azo compounds, air bubbles, etc.), surfactants, or additives described below, in an amount of, for example, 0 to 5 mass % and preferably 0 to 1 mass % to improve the various physical properties of a water absorbent resin or particulate water absorbent agent to be obtained. A graft polymer obtained by using other components (e.g., starch-acrylic acid graft polymer) or a water absorbent resin composition is also generically referred to as a polyacrylic acid (salt)-type water absorbent resin in the present invention.

As the additive, a chelating agent, hydroxycarboxylic acid, or a reducing inorganic salt may be added, and it may be added to the water absorbent resin in such a manner that the amount thereof is preferably 10 to 5000 ppm by mass, more preferably 10 to 1000 ppm by mass, still more preferably 50 to 1000 ppm by mass, and particularly preferably 100 to 1000 ppm by mass. A chelating agent is preferable to be used.

The monomer is also preferable to contain a polymerization inhibitor. Examples of the polymerization inhibitor include such as methoxyphenol etc., and the content thereof is preferably 200 ppm or lower, more preferably 10 to 160 ppm, and still more preferably 20 to 100 ppm (relative to monomer).

(f) Polymerization Step (Crosslinking Polymerization Step)

Owing to the performance and the easiness of polymerization control, the polymerization method may be carried out by spray polymerization or droplet polymerization, but preferably, in general, it is carried out by aqueous solution polymerization or reverse phase suspension polymerization. The aqueous solution polymerization is preferably which are conventionally difficult to control polymerization or improve the coloring, and further preferably continuous aqueous solution polymerization. An especially preferable controlling method is a continuous polymerization method for producing the water absorbent resin in a huge scale of 0.5 t/h or higher, further 1 t/h or higher, still more 5 t/hr or higher, and still further 10 t/hr or higher by polymerization of an aqueous unsaturated monomer solution in one line. Consequently, the preferable continuous polymerization may include methods described as continuous kneader polymerization (e.g. U.S. Pat. Nos. 6,987,151 and 670,141), continuous belt polymerization (e.g. U.S. Pat. Nos. 4,893,999 and 6,241,928, and US Patent Application Publication No. 2005/215734).

In addition, in the continuous polymerization, polymerization at a high temperature starting (monomer at 30° C. or higher, 35° C. or higher, further 40° C. or higher, and particularly 50° C. or higher: the upper limit is the boiling point) or a high monomer concentration (30 mass % or higher, 35 mass % or higher, further 40 mass % or higher, and particularly 45 mass % or higher: the upper limit is the saturated concentration) can be exemplified as one preferable example.

The monomer stability is excellent in the present invention and the water absorbent resin with white color can be obtained even by the polymerization in such a high concentration and at such a high temperature, and thus the effect is significantly exhibited in such conditions. Preferable examples of high temperature initiating polymerization are described in U.S. Pat. Nos. 6,906,159 and 7,091,253 etc. In the present invention, the monomer stability before polymerization is excellent and therefore, production in an industrial scale is made easy.

The polymerization can be carried out in atmospheric air; however, it is preferable for coloring improvement to carry out the polymerization in an inert gas atmosphere of nitrogen or argon (e.g., oxygen concentration of 1% by volume or lower) and also, the monomer is preferable to be used for polymerization after the dissolved oxygen in the monomer or the solution containing the monomer is sufficiently replaced with an inert gas (e.g., less than 1 mg/L of dissolved oxygen). Even if such degassing is carried out, the monomer is excellent in the stability and therefore gelatinization before the polymerization does not occur and the water absorbent resin with higher physical properties and high whiteness can be obtained.

(g) Polymerization Initiator

A polymerization initiator to be used for the present invention can be selected properly in accordance with the polymerization mode. Examples of the polymerization initiator may include radical polymerization initiator such as a photodecomposition type polymerization initiator, a heat decomposition type polymerization initiator, and a redox type polymerization initiator. The amount of the polymerization initiator may be 0.0001 to 1% by mole preferably and more preferably 0.001 to 0.5% by mole to the monomer.

In the case of the amount of the polymerization initiator is large, coloring may possibly generate and in the case of the amount is low, it results in increase of the residual monomer. Further, in the case of a conventional color-improve agent, it sometimes causes a negative effect on the polymerization; however, in the polymerization by the method of the invention, the coloring can be improved without causing any negative effect and therefore, it is preferable.

Examples of the photodecomposition type polymerization initiator may include benzoin derivatives, benzyl derivatives, acetophenone derivatives, benzophenone derivatives, and azo compounds. Examples of the heat decomposition type polymerization initiator may include persulfuric acid salts (sodium persulfate, potassium persulfate, and ammonium persulfate), peroxides (hydrogen peroxide, tert-butyl peroxide, methyl ethyl ketone peroxide), azo compounds (2,2'-azobis (2-amindinopropane)dihydrochloride, 2,2'-azobis[2-(2-imidazolin-2-yl)propane]dihydrochloride, etc.). Among these radical polymerization initiators, persulfuric acid salts, peroxides, and azo compounds can be used as a photopolymerization initiator.

Examples of the redox type polymerization initiator may include the above-mentioned persulfuric acid salts or peroxides in combination with reducing compounds such as L-ascorbic acid and sodium hydrogen sulfite. Further, combination use of a photodecomposition type initiator and a heat decomposition type polymerization initiator can also be exemplified as a preferable embodiment.

(2) Gel Shredding Step (Pulverization Step)

A hydrous gel-like crosslinked polymer obtained by polymerization (hereinafter, sometimes referred to as "hydrous gel") may be dried as it is; however, it may be pulverized to be particulate (e.g., with a mass average particle diameter of 0.1 to 5 mm, preferably 0.5 to 3 mm) during polymerization or after polymerization with a pulverizer (kneader, meat chopper, or the like) if necessary.

From the physical property aspect, regarding the temperature of the hydrous gel at the time of gel pulverizing, the hydrous gel is kept or heated preferably at 40 to 95° C. and more preferably 50 to 80° C. The resin solid content of the hydrous gel is not particularly limited; however, from the physical property aspect, it is preferably 10 to 70 mass %, more preferably 15 to 65 mass %, and still more preferably 30 to 55 mass %. It is optional to add water, a polyhydric alcohol, a mixed liquid of water and a polyhydric alcohol, a solution obtained by dissolving a polyvalent metal in water, or their vapor, or the like. In the gel shredding step, a water absorbent resin fine powder or various kinds of other additives may be kneaded.

(3) Drying Step

In order to accomplish a decrease in residual monomers, prevention of gel deterioration (urea resistance), and prevention of yellowing in the present invention, the drying step is carried out via the gel shredding step after, completion of the polymerization. The time until the start of drying via the gel shredding step is more preferable as it is shorter. That is, after being discharged out of the polymerization apparatus, a hydrous gel-like crosslinked polymer after polymerization starts to be dried preferably within 1 hour, more preferably within 0.5 hours, and still more preferably within 0.1 hours (charged to a drier). In order to set the time within the range, shredding or drying is preferably carried out directly without carrying out a storage step for the gel after polymerization. Further, to decrease the residual monomer and accomplish low coloring, the temperature of the a hydrous gel-like crosslinked polymer from completion of the polymerization to starting of the drying is controlled preferably at 50 to 80° C. and more preferably at 60 to 70° C.

The drying step provides a dried product having a resin solid content, which is calculated from a drying loss of the polymer (drying of 1 g powder or particles at 180° C. for 3 hours) in an amount controlled to be preferably 80 mass % or higher, more preferably 85 to 99 mass %, still more preferably 90 to 98 mass %, and particularly preferably 92 to 97 mass %. The drying temperature is not particularly limited; however, it is preferably in a range of 100 to 300° C. and more preferably in a range of 150 to 250° C. To satisfy both of the high physical properties and whiteness, it is preferably that the drying temperature is 160 to 235° C., more preferably 165 to 230° C. Further the drying time is preferably within 50 minutes. If the temperature or the time is out of the above-mentioned range, it may possibly result in decrease of the water absorption rate (CRC), increase of soluble matters (Extractables), and deterioration of whiteness index.

A various drying methods such as heat drying, hot-air drying, vacuum drying, infrared drying, microwave drying, drying by a drum drier, azeotropic dehydration with a hydrophobic organic solvent, high humidity drying using high temperature steam can be employed. It is preferably hot-air drying with a gas with a dew point of preferably 40 to 100° C. and more preferably 50 to 90° C.

(4) Crushing and Classifying Step (Particle Size Adjustment After Drying)

After the drying step, the above-mentioned a hydrous gel-like crosslinked polymer, the particle size may be adjusted after the drying if necessary. The polymer is preferably made to have a specified particle size to improve the physical properties by surface crosslinking described below. The particle size can be adjusted properly by polymerization (particularly reversed phase suspension polymerization), crushing, classification, granulation, and fine powder recovery. Hereinafter, the particle size is defined by a standard sieve (JIS Z8801-1 (2000)).

The mass average particle diameter (D50) of the obtained water absorbent resin particles in the dried step before surface crosslinking is adjusted to be 200 to 600 µm, preferably 200 to 550 µm, more preferably 250 to 500 µm, and particularly preferably 350 to 450 µm. It is more preferable as the particles smaller than 150 µm are less, and the particles are adjusted in a range of generally 0 to 5 mass %, preferably 0 to 3 mass %, and more preferably 0 to 1 mass %. Further, it is more preferable as the particles bigger than 850 µm are less, and the particles are adjusted in a range of generally 0 to 5 mass %, preferably 0 to 3 mass %, and more preferably 0 to 1 mass %. The logarithmic standard deviation ($\sigma\zeta$) of the particle size distribution is preferably 0.20 to 0.40, more preferably 0.25 to 0.37, and particularly preferably 0.27 to 0.35. Its measurement method may be a method described in, for example, International Publication No. 2004/69915 and a method described in EDANA-ERT 420.2-02 by using a standard sieve. The particle diameter is preferably applied also to the finally obtained water absorbent resin after surface crosslinking.

In general if the particle size distribution is narrowed, that is, the upper and lower limits of the particle size are controlled to be narrow, the color becomes noticeable; however, the present invention is free from such color issue and is preferable. Accordingly, in the present invention, it is preferable to carry out a classification step to give the ratio of particles with 150 to 850 µm of 90 mass % or more, more preferably 95 mass % or more, particularly preferably 98 mass % (The upper limit is 100 mass %) or more, after drying.

The bulk specific gravity of the water absorbent resin particles is preferably 0.5 to 0.75 (g/cm$^3$) and more preferably 0.6 to 0.7 (g/cm$^3$). A measurement method thereof is described in detail in, for example, EDANA ERT 460.2-02. In the case where the bulk specific gravity is not satisfied, the stirring power index becomes difficult to be controlled or the physical properties may be lowered or powdering may be caused in some cases.

(5) Surface Treatment Step

The method for producing a water absorbent resin of the present invention is such that the water absorbent resin obtained through, for example, (1) to (4), is subjected to a heat surface-crosslinking step and a specified cooling step.

The present invention provides;

a method for producing a polyacrylic acid (salt)-type water absorbent resin, comprising steps of:

preparing an aqueous monomer solution of acrylic acid (salt), polymerizing the aqueous monomer solution, finely shredding a hydrous gel-like type crosslinked polymer during or after polymerization, drying the obtained particulate a hydrous gel-like crosslinked polymer, crushing the dried product, classifying the dried product, heating and surface-crosslinking the dried product after the classification, and cooling after the surface-crosslinking, wherein a refrigerant of a cooling apparatus of the cooling step is heated to the temperature higher than a dew point of a gas introduced in the cooling apparatus, and/or, the inner surface area of a cooling apparatus to be used in the cooling step is 0.25 to 0.95 times as large as the inner surface area of a heating apparatus to be used in the heating and surface-crosslinking step.

Hereinafter, the method will be further described.

(5-1) Humidifying and Mixing Step

This humidifying and mixing step is a step of adding and mixing a surface-crosslinking agent to and with the water absorbent resin powder obtained through the polymerization step to the classification step.

(a) Surface-Crosslinking Agent

The present invention further includes a surface-crosslinking step after drying. The production method of the present invention is preferably applicable for a method for producing a water absorbent resin with high absorption against pressure (AAP) and liquid permeability (SFC) and continuous manufacture in a huge scale (particularly 1 t/hr), and particularly preferably applicable for high temperature surface-crosslinking of a water absorbent resin.

Treatment agents described in Patent Documents 1 to 19, particularly surface-crosslinking agents, are used for the surface treatment in the present invention. From the viewpoints of physical properties at the time of scale-up, covalent bonding surface-crosslinking agents are used among them, and preferably covalent bonding surface-crosslinking agents and ion bonding surface-crosslinking agents are used in combination.

(Covalent Bonding Surface-Crosslinking Agent)

Examples of a surface crosslinking agent to be employed in the present invention may include various organic or inorganic crosslinking agents, and organic surface crosslinking agents are preferably used. From the viewpoints of physical properties of obtained water absorbent resin, preferable examples to be used as the surface crosslinking agent are polyhydric alcohol compounds, epoxy compounds, polyamine compounds and their condensation products with haloepoxy compounds, oxazoline compounds (mono-, di-, or poly-)oxazolidinone compounds, and alkylene carbonate compounds. Particularly dehydration reactive crosslinking agents containing polyalcohol compounds, alkylene carbonate compounds, and oxazolidinone compounds, which require a high temperature reaction, are usable. In the case where no dehydration reactive crosslinking agent is used, the physical properties may sometimes be inferior or the difference of the effects of the present invention may sometimes be hard to be caused in some cases.

More concretely, examples are compounds exemplified in U.S. Pat. Nos. 6,228,930, 6,071,976, and 6,254,990. Examples are polyalcohol compounds such as mono-, di-, tri-, or tetra-propylene glycol, 1,3-propanediol, glycerin, 1,4-butanediol, 1,3-butanediol, 1,5-pentanediol, 1,6-hexanediol, sorbitol, etc.; epoxy compounds such as ethylene glycol diglycidyl ether, glycidol, etc.; alkylene carbonate compounds such as ethylene carbonate; oxetane compounds; and cyclic urea compounds such as 2-imidazolidinone.

(Ion-Bonding Surface Crosslinking Agent)

Further, other than the above-mentioned organic surface crosslinking agent, an ion-bonding inorganic surface crosslinking agent (crosslinking agent derived from polyvalent metal) may be used to improve the liquid permeability potential or the like. Examples usable as the inorganic surface crosslinking agent may include divalent or higher, preferably, trivalent to tetravalent polyvalent metal salts (organic salts and inorganic salts) and hydroxides. Polyvalent metals to be used are aluminum, zirconium, etc., and aluminum lactate and aluminum sulfate are usable. These inorganic surface crosslinking agents may be used simultaneously with or separately from the organic surface crosslinking agent. The surface crosslinking with polyvalent metals is exemplified in International Publication Nos. 2007/121037, 2008/09843, and 2008/09842, in U.S. Pat. Nos. 7,157,141, 6,605,673, and 6,620,889, in US Patent Application Publication Nos. 2005/0288182, 2005/0070671, 2007/0106013, and 2006/0073969.

Further, other than the above-mentioned organic surface crosslinking agent, a polyamine polymer, particularly, having a mass average molecular weight of about 5000 to 1000000 may be used simultaneously or separately to improve the liquid permeability potential and the like. Usable polyamine polymers are exemplified in U.S. Pat. No. 7,098,284, International Publication Nos. 2006/082188, 2006/082189, 2006/082197, 2006/111402, 2006/111403, and 2006/111404 etc.

(The Use Amount)

The use amount of the surface crosslinking agent is preferably 0.001 to 10 parts by mass and more preferably 0.01 to 5 parts by mass relative to 100 parts by mass of the water absorbent resin particles. Water can be preferably used in combination with the surface crosslinking agent. The amount of water to be used is preferably in a range of 0.5 to 20 parts by mass and more preferably 0.5 to 10 parts by mass relative to 100 parts by mass of the water absorbent resin particles. In the case of using the inorganic surface cross-linking agent and the organic surface crosslinking agent in combination, the agents are used preferably in a range of 0.001 to 10 parts by mass and more preferably 0.01 to 5 parts by mass, respectively.

Further, at that time, a hydrophilic organic solvent may be used and its amount is in a range of 0 to 10 parts by mass and preferably 0 to 5 parts by mass relative to 100 parts by mass of the water absorbent resin particles. Still more, at the time of mixing a cross-linking agent solution with the water absorbent resin particles, a water insoluble fine particle powder, and a surfactant may coexist to an extent that the effect of the present invention is not hindered, that is, in a range, for example, of 0 to 10 parts by mass, preferably 0 to 5 parts by mass, and more preferably 0 to 1 part by mass. The surfactant to be used and its use amount are exemplified in U.S. Pat. No. 7,473,739 etc.

(b) Mixing Apparatus

Figure 4:
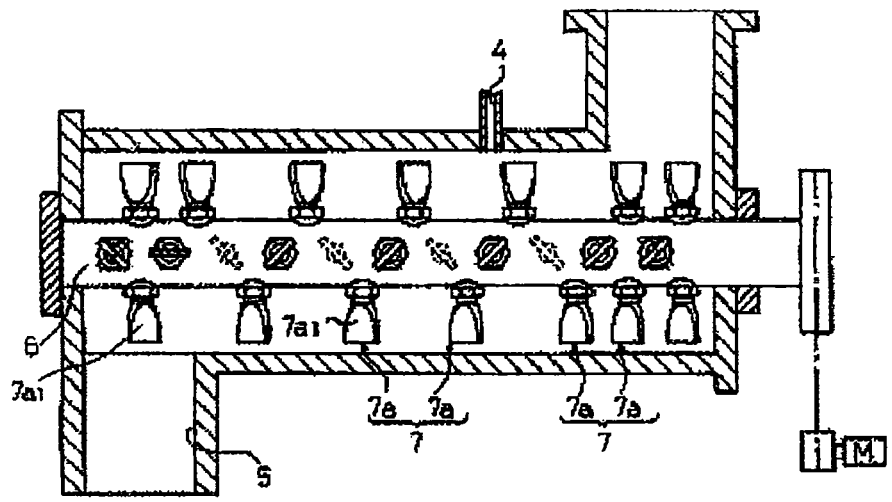
FIG. 4 is a cross-sectional view showing one example of a high speed rotation stirring type mixing apparatus usable for mixing a surface-crosslinking agent. Reference numeral 2 represents an inner wall, 6 represents a stirring shaft, and 7 (7a, 7b) represents stirring blades.
Figure 5:
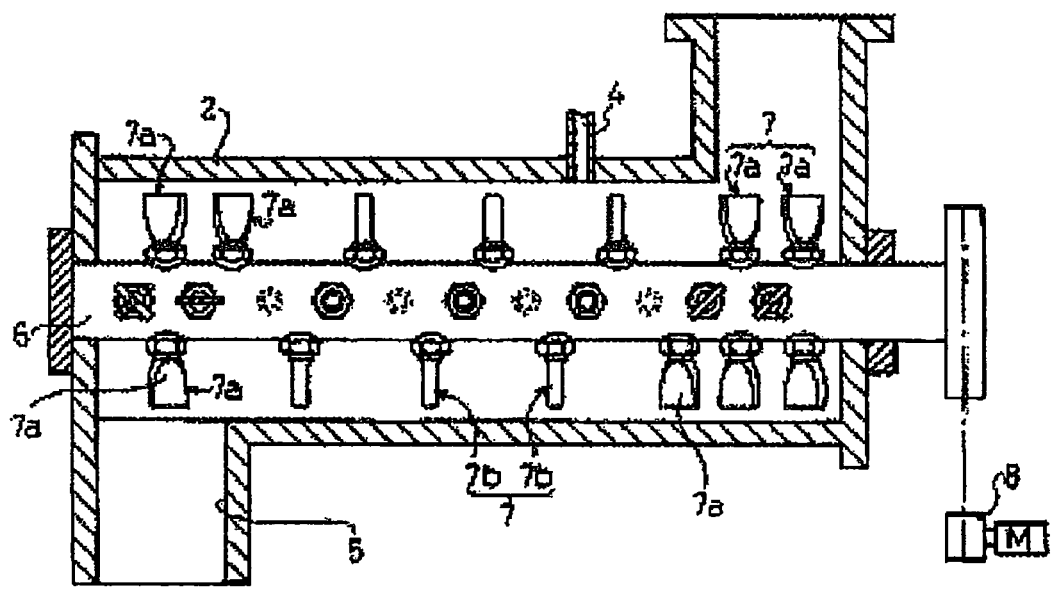
FIG. 5 is a cross-sectional view showing one example of a high speed rotation stirring type mixing apparatus usable for mixing a surface-crosslinking agent. Reference numeral 2 represents an inner wall, 6 represents a stirring shaft, and 7 (7a, 7b) represents stirring blades.

In the present invention, for mixing the surface treatment agent, a continuous high speed rotation stirring type mixing apparatus is used. Especially, a transverse type continuous high speed rotation stirring type mixing apparatus (e.g., FIG. 4 and FIG. 5) is preferable. In addition, the surface treatment agent refers to the above-mentioned surface-crosslinking agent, or a substituent thereof (e.g., a radical polymerization initiator such as a persulfuric acid salt and a monomer) and is also a concept including a solution or dispersion liquid thereof. The stirring speed is preferably 100 to 10000 rpm and more preferably 300 to 2000 rpm. The retention time is within 180 seconds, more preferably 0.1 to 60 seconds, and particularly preferably 1 to 30 seconds.

(c) Temperature of Water Absorbent Resin Before Surface-Crosslinking

In the present invention, the temperature of water absorbent resin particles (e.g., a water absorbent resin in which it is mixed with the surface-crosslinking agent and then before it is introduced into the surface-crosslinking step; the resin is also referred to as a particulate water absorbent agent) to be supplied to the surface-crosslinking step or to a transportation tube is preferably 30° C. or higher, more preferably 40° C. or higher, and still more preferably 50° C. or higher. The upper limit thereof is preferably 100° C. and more preferably 95° C. Deterioration of the physical properties of the water absorbent resin particles (particulate water absorbent agent) can be suppressed by keeping the temperature of the particulate water absorbent resin to be supplied to a transportation tube at a prescribed temperature or higher. Specifically, a significant effect is caused on maintain of the physical properties such as saline flow conductivity (SFC).

(5-2) Heat Treatment Step

This heat treatment step is a step of heating the wet mixture of a water absorbent resin powder and a surface treatment agent solution mixed in the humidifying and mixing step to cause surface-crosslinking reaction.

(a) Structure of Heating Apparatus (Heating Apparatus)

A heating apparatus to be used in the present invention is preferably a continuous type apparatus and examples thereof include a groove type mixing and drying apparatus, a rotary drier, a disk drier, a fluidized bed drier, a flash drier, an infrared drier, a paddle drier, and a vibrating and fluidizing drier. From the viewpoints of improvement of physical properties and stabilization, a paddle drier is preferable.

(Stirring Power Index)

As the continuous heating apparatus used in the present invention, it is preferable to use a transverse type continuous stirring apparatus (e.g., FIG. 1) having a charging inlet and a discharge outlet for a water absorbent resin, as well as a stirring means including one or more (preferably a plurality) of rotary shafts equipped with a plurality of stirring disks and a heating means.

At the time of crosslinking reaction, the stirring power index is preferable to set to 3 to 15 W·hr/kg. Herein, the stirring power index is defined as (stirring power index)= ((power consumption of apparatus at the time of surface treatment)−(power consumption at the time of idling)×average retention time)/(treatment amount per unit time×average retention time), and a water absorbent resin with high physical properties can be continuously and stably obtained even at the time of scale-up to a large scale (particularly, 1 t/hr or more) based on a specified apparatus and specified parameters thereof (stirring power index).

The stirring power index can be easily calculated as described above from the power consumption of apparatus at the time of surface treatment and the power consumption at the time of idling. If this stirring power index exceeds 15 W·hr/kg, the physical properties (particularly, liquid permeability) are deteriorated and on the other hand, if it is under 3 W·hr/kg, the physical properties (particularly, water absorption against pressure) are also deteriorated. The stirring power index is more preferably in a range of 4 to 13 W·hr/kg, still more preferably 5 to 11 W·hr/kg, particularly preferably 5 to 10 W·hr/kg, and most preferably 5 to 9 W·hr/kg.

The stirring power index can be determined properly in consideration of adjustment of the supply amount and discharge amount of the water absorbent resin, the particle size or bulk specific gravity of the water absorbent resin, the rotation speed and shape of the apparatus, the composition of the surface treatment agent, and the retention time, and the followings are preferable conditions.

(Inclined Angle)

Heat treatment is carried out for the water absorbent resin after the surface treatment agent is added to the stirring apparatus. The transverse type continuous stirring apparatus is a necessary apparatus. In terms of control of the stirring power index, the transverse type continuous stirring apparatus is preferable to have a downward inclined angle of 0.1 to 10°. The inclined angle is more preferably 0.5 to 5° and still more preferably 1 to 4°. In the case where the inclined angle does not satisfy the range, the stirring power index becomes too high or too low and the physical properties of the water absorbent resin may possibly be deteriorated in some cases.

(Aspect Ratio)

The aspect ratio (length of apparatus in movement direction/width of apparatus of cross section to movement direction) of the transverse type continuous stirring apparatus is preferably 1 to 20. The aspect ratio is more preferably 1.5 to 10 and still more preferably 2 to 5. The aspect ratio is determined as the ratio of the vertical (movement direction) length and the transverse (perpendicular to the movement direction in a plane) length in the inside of the apparatus. In the case where the aspect ratio does not satisfy the range, the stirring power index becomes too high or too low and the physical properties of the water absorbent resin may possibly be deteriorated in some cases or the piston flow property in the apparatus may be sometimes worsened and the stability of the performance may be worsened in some cases.

(Scraping Blades)

Figure 2:
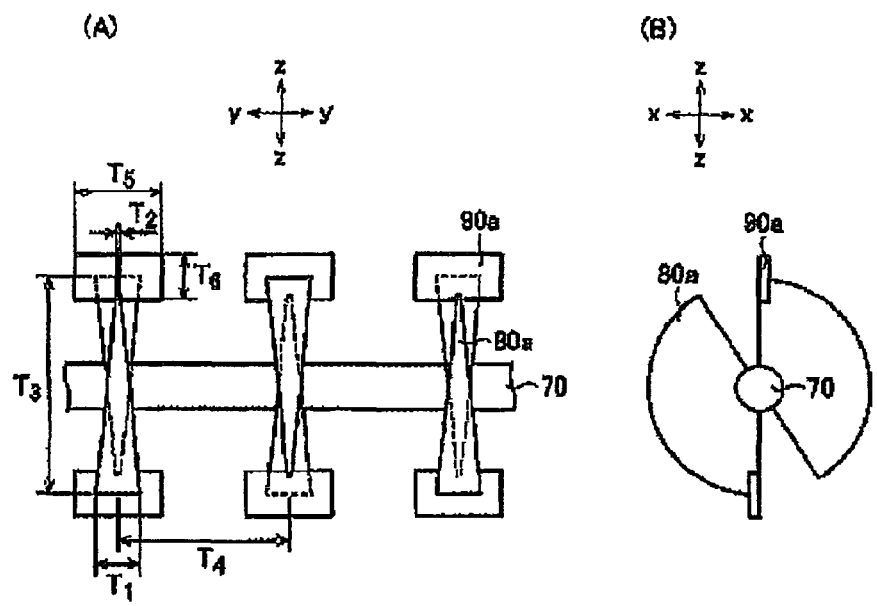
FIG. 2 is a cross-sectional view showing one example of a stirring disk (equipped with scraping blades) of a biaxial heating apparatus or cooling apparatus.

The transverse type continuous stirring apparatus is preferable to have scraping blades (the scraping blades are denoted, for example, by 90a in FIG. 2). The scraping blades are described in Patent Document 31 (JP-A No. 2004-352941). If the scraping blades are used, the stirring power index can be controlled to be low and as a result, the physical properties of the water absorbent resin can be improved.

(Average Retention Time)

In terms of control of the stirring power index within the preferable range, the average retention time of the water absorbent resin is preferably controlled to be 0.05 to 2 hours. The average retention time is more preferably 0.1 to 1 hour and still more preferably 0.2 to 0.8 hours.

The average retention time measurement for the water absorbent resin in the transverse type continuous stirring apparatus of the present invention will be described. The retention time in the apparatus (also known as heating time or reaction time in the transverse type continuous stirring apparatus) is controlled by various factors such as effective volume of the apparatus (in the case where there is a stirring shaft arranged in the transverse direction, the effective volume refers to the volume covering the upper most surface of a stirring disk as the apex (see FIG. 1): the inner volume in the present invention), the amount of the water absorbent resin particles to be supplied, inclined angle, the rotation speed of the stirring shaft, the shape of the scraping blade, the bulk specific gravity of the water absorbent resin particles, the kind of the surface treatment agent, the height of the discharge bank installed in the discharge outlet of the transverse type continuous stirring apparatus. These factors considerably affect not only the retention time but also the stirring power index. A method of measuring the average retention time is carried out by actually operating the apparatus under the condition in which the various factors are fixed and measuring the mass of the water absorbent resin particles remaining in the apparatus after stopping the operation of the apparatus. Alternatively, the average retention time can also be determined by unsteadily introducing a substance easy to be identified (for example, a compound containing sulfur) into the charging inlet of the apparatus as a tracer substance, tracing the concentration fluctuation of the substance at the discharge outlet, obtaining the retention time distribution function, and carrying out calculation according to the retention time distribution function. As the tracer substance, for example, a water-soluble sulfuric acid salt can be used. Further, as a concentration analysis method, there is a method of tracing the concentration fluctuation by measuring the intensity ratio of the characteristic x-ray of sulfur and a monovalent cation (e.g., sodium) with EPMA, XMA, or the like in the case of a partially neutralized polyacrylic acid water absorbent resin. The retention time distribution function and the average retention time are described in detail in "Introduction of Chemical Reaction Engineering (Hannou Kogaku Gairon)", Hiroshi KUBOTA, issued by the Nikkan Kogyo Shimbun, Ltd.

(Surface Roughness)

The inside of the transverse type continuous stirring apparatus is preferably smooth and the surface roughness (Rz) thereof is controlled to be 800 nm or lower preferably. The surface roughness (Rz) is preferably 500 nm or lower, more preferably 300 nm or lower, still more preferably 200 nm or lower, particularly preferably 185 nm or lower, and most preferably 170 nm or lower. In the case where the surface roughness (Rz) of the inside of the transverse type continuous stirring apparatus does not satisfy the range, since the friction resistance with the water absorbent resin particles becomes high, the stirring power index becomes too high and the physical properties may possibly be deteriorated.

The surface roughness (Rz) means the value of the maximum height of the surface unevenness and is defined according to JIS B 0601-2001. The lower limit of the surface roughness (Rz) is 0 nm; however, there is not so much difference in the case where it is about 10 nm, and about 20 nm is satisfactory.

From the above-mentioned viewpoint, a material for the transverse type continuous stirring apparatus is preferably stainless steel and more preferably obtained by mirror finishing. The mirror finishing suppresses damage on the water absorbent resin powder. Examples of the stainless steel to be used for the apparatus include SUS 304, SUS 316, and SUS 316L.

The surface roughness (Ra) other than the surface roughness (Rz) is also defined according to JIS B0601-2001 and a preferable value thereof is also the same as that of the surface roughness (Rz). The surface roughness (Ra) is preferably 250 nm or lower and more preferably 200 nm or lower. These surface roughness values may be measured according to JIS B 0651-2001 by a probe type surface roughness meter. The surface roughness can be applied not only for the heating apparatus but also for apparatuses before and after the heating apparatus, preferably, for a cooling apparatus, a transportation pipe (particularly, a pneumatic transportation pipe) and a hopper, and the effect of improving physical properties by surface-crosslinking can be heightened.

(Rotary Shaft and Stirring Disk)

The transverse type continuous stirring apparatus has one or a plurality of rotary shafts, preferably 2 to 10 rotary shafts, and particularly 2 shafts. Further, the number of a stirring disk (e.g., in FIG. 2) or a stirring blade may be determined properly in accordance with the size (capacity) of the apparatus, and it is preferably 2 to 100 disks and more preferably 5 to 50 disks per one shaft.

(Periodical Shielding)

In terms of physical property stability and improvement by surface-crosslinking, it is preferable to periodically shield the transverse type continuous high speed rotation stirring type mixing apparatus and the transverse type stirring apparatus after the water absorbent resin and the surface treatment agent solution are mixed to be introduced into the stirring apparatus. The interval for the periodical shielding is preferably 0.001 to 5 minutes, more preferably 0.005 to 1 minute, still more preferably 0.01 to 0.1 minutes, and particularly preferably 0.01 to 0.05 minutes. Execution of the periodical shielding makes it possible to carry out periodic introduction of the water absorbent resin into the continuous apparatus installed downstream (introduction of the water absorbent resin into a heating apparatus from a mixing apparatus or into a cooling apparatus from a heating apparatus); that is, the introduction is turned on and off intermittently. In the case where no periodic shielding is carried out in the surface-crosslinking step, the physical properties of a water absorbent resin to be obtained may possibly be deteriorated in some cases. The shielding ratio (the ratio of the time when the water absorbent resin is shielded from the continuous apparatus installed downstream) is preferably in a range of 1 to 80%, more preferably 2 to 40%, still more preferably 5 to 30%, particularly preferably 5 to 20%, and most preferably 5 to 10%, in terms of stabilization of the physical properties (standard deviation). It is sufficient that the water absorbent resin in the above amount range (e.g., 1 t/hr or more) is fed to a next apparatus even if the periodical shielding is executed. For example, in the case of a rotary valve, the shielding interval is defined as the reciprocal number (minute) of the rotation speed (rpm), and the shielding ratio is defined as a value calculated by dividing the theoretical rotation speed (rpm) per one minute of the rotary valve needed for discharging a mixture (wet powder; a mixture of the water absorbent resin and the surface-crosslinking agent solution) to be supplied to the continuous high speed mixing apparatus (theoretical rotation speed is obtained from the volume flow rate calculated from the volume per one rotation of the rotary valve, the mass flow rate of the mixture to be discharged, and the bulk specific gravity) by actual rotation speed (rpm) of the rotary valve, and multiplying the calculated value by 100. The shielding ratio is specifically defined as a value calculated by dividing the rotation speed (rpm) per one minute of the rotary valve needed for discharging a wet powder (a mixture of the water absorbent resin and the surface-crosslinking agent) out of a mixing apparatus per unit time by the actual rotation speed of the rotary valve. It is calculated, for example, in the case of the example of the present invention as 1500×(1+3.5/100)/0.47/1000/0.02/60/25×100=11.0%.

The amount of the water absorbent resin retained by periodical shielding is preferably 0 to 2 mass % and more preferably exceeding 0 and to 1 mass % relative to the treatment amount. The volume per one rotation of the rotary valve may be determined properly and it is preferably 0.1 to 0.001 [m³/lev (one rotation)], more preferably 0.2 to 0.002 [m³/lev], and still more preferably 0.1 to 0.01 [m³/lev]. In the case where the periodic shielding is carried out or even when the periodic shielding is no carried out, when the continuous apparatuses (the mixing apparatus, the heating apparatus, and the cooling apparatus if necessary) are joined, the distance from the outlet of an upstream apparatus and the inlet of an apparatus installed downstream is preferably 10 m or shorter. The distance is more preferably 5 m or shorter, still more preferably 3 m or shorter, and particularly preferably 2 m or shorter. At the time of joining these apparatuses, the apparatuses are joined up and down; that is, the downstream apparatus is joined to a lower side of the upstream apparatus. A shielding apparatus of the water absorbent resin particles may be installed between the upstream apparatus and the downstream apparatus. The lower limit of the distance may be determined properly in accordance with the sizes of the apparatuses or in a range in which a shielding apparatus described below can be housed. In the case where the distance is too large or the apparatuses are not joined up and down, the physical properties of a water absorbent resin to be obtained may possibly be deteriorated in some cases. In the case of joining up and down, the mixing apparatus, the heating apparatus, and the cooling apparatus if necessary may be joined up and down in this order. Joining of the cooling apparatus may be above or beside the heating apparatus.

Figure 3:
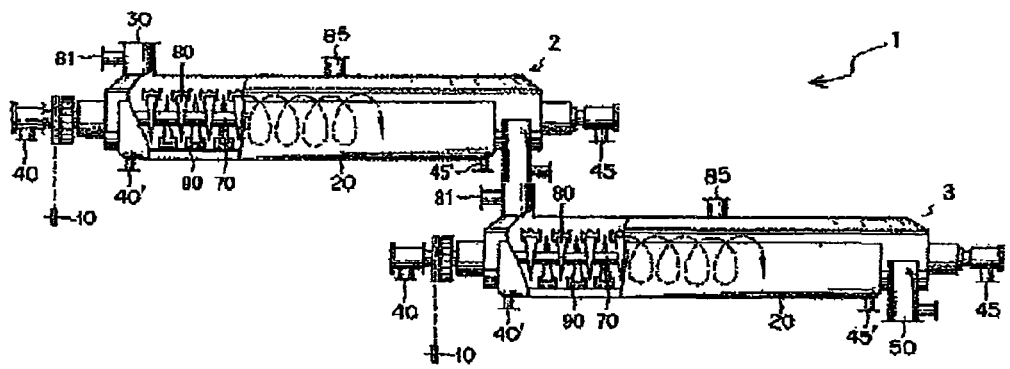
FIG. 3 is a schematic view of the vertical cross section of a heating apparatus and a cooling apparatus having a joined biaxial transverse type continuous stirring apparatus. Herein, the heating apparatus or the cooling apparatus is an apparatus having a similar shape with the same inner area (inner volume) and can correspond to conventional techniques.

A gate, a valve, a damper, a rotary feeder, a table feeder, or the like is installed as a periodically shielding apparatus in a joining part of the continuous apparatuses so that the periodical shielding can be carried out. Examples of the gate to be employed include a slide gate, a roller gate, a tainter gate, a radial gate, a flap gate, a rolling gate, and a rubber gate etc. Examples of the valve to be employed include a Howell-Bunger (fixed cone dispersion) valve, a hollow jet valve (a movable cone dispersion valve), a jet flow valve, a butterfly valve, a gate valve (a partition valve), an orifice valve, a rotary valve (a valve for opening or closing by rotating a cylinder), and a Johnson valve (a valve for opening or closing by moving a conical valve body back and forth). These shielding apparatuses may be installed in an outlet of the mixing apparatus, or in an inlet of the heating apparatus, or in a middle part thereof after the outlet of the mixing apparatus and the inlet of the heating apparatus (e.g., FIG. 1) are joined. The periodic shielding is also similarly carried out preferably between an outlet of the heating apparatus (e.g., FIG. 1) and the cooling apparatus (e.g., FIG. 3). The shielding and joining of the apparatuses are preferably carried out via a valve, particularly a rotary valve, among these shielding apparatuses. The size (it refers to diameter: however, in the case where the cross section is other than a circular shape, it is converted into the diameter of a circle with the same surface area) of the valve may be selected properly and it is preferably, for example, 1 to 100 cm in diameter and more preferably 10 to 50 cm in diameter.

Each shielding apparatus is operated at less than 100% of the maximum treatment amount defined by the amount of the water absorbent resin supplied per one time (kg/hr; the maximum amount of a substance which can be passed through the shielding apparatus per unit time). The operation condition is preferably 5 to 95%, more preferably 10 to 90%, and still more preferably 20 to 80%. In the case where the operation condition of the shielding apparatus is out of the above-mentioned range, the physical properties of a water absorbent resin to be obtained may possibly be deteriorated in some cases and the performance may possibly become unstable. In the case where a rotary shielding apparatus such as a rotary valve is used, the rotation speed thereof may be determined properly and it is preferably 1 to 500 rpm (rotation/minute). The rotation speed is more preferably 5 to 200 rpm, still more preferably 10 to 100 rpm, and particularly preferably 20 to 100 rpm. The maximum treatment performance of the shielding apparatus may be determined properly and it is, for example, preferably 0.01 to 20 t/hr and more preferably 0.1 to 5 t/hr.

(b) Operation Condition of Heating Apparatus

After the surface treatment agent is added to the stirring type mixing apparatus (e.g., FIG. 4 and FIG. 5) and the water absorbent resin and the surface treatment agent solution are mixed, heat surface-crosslinking treatment is carried out. The transverse type continuous stirring apparatus (e.g., FIG. 1) is preferably an apparatus necessary for heating treatment. The water absorbent resin is treated by heat treatment and is also treated by second heat treatment if necessary, and thereafter is treated by cooling treatment. The heating temperature (heat transfer surface temperature of a jacket or the like) is 70 to 300° C., preferably 120 to 250° C., and more preferably 150 to 250° C., and the heating time is preferably in a range of 1 minute to 2 hours. The heat treatment is carried out generally by a drier or a heating furnace. The present invention can provide a water absorbent resin with high whiteness even by high temperature heating or drying with air (hot blow) which conventionally causes intense coloration.

(Filling Ratio)

It is preferable to continuously supply the water absorbent resin in such a manner that the filling ratio (volume ratio) of the transverse type continuous stirring apparatus with the water absorbent resin can be 50 to 90%. The filling ratio is more preferably 55 to 85% and still more preferably 60 to 80%. In the case where the filling ratio does not satisfy the above-mentioned range, the stirring power index is hard to be controlled, and the physical properties of a water absorbent resin to be obtained may possibly be deteriorated in some cases. The position at 100% filling ratio is the apex part of a stirring disk of a rotary shaft as described above.

It is preferable to continuously supply the water absorbent resin in such a manner that the mass surface area ratio of the water absorbent resin in the transverse type continuous stirring apparatus can be 100 kg/m²/hr or lower. It is more preferably 90 kg/m²/hr or lower and still more preferably 50 to 70 kg/m²/hr. In the case where the mass surface area ratio does not satisfy the above-mentioned range, the stirring power index is hard to be controlled and the physical properties of a water absorbent resin to be obtained may possibly be deteriorated in some cases.

Herein, the mass surface area ratio is defined by the following equation.

(Mass surface area ratio)=(Mass flow rate of water absorbent resin per unit time)/(Heat transfer area of apparatus)

In the case where the jacket surface of an apparatus trough is only for heat insulation, the mass surface area ratio is defined as follows.

(Mass surface area ratio)=(Mass flow rate of water absorbent resin per unit time)/(Heat transfer area of stirring shaft and stirring disk of apparatus)

(Rotation Speed and Reaction Time)

According to the present invention, uniform heating and mixing can be carried out by adjusting the stirring speed of the transverse type continuous stirring apparatus to 2 to 40 rpm. If it is lower than 2 rpm, the stirring becomes insufficient and on the other hand, if it is higher than 40 rpm, a fine powder tends to be generated easily in some cases. The stirring speed is more preferably 5 to 30 rpm. The retention time in the apparatus is, for example, 10 to 180 minutes and more preferably 20 to 120 minutes. If it is shorter than 10 minutes, the crosslinking reaction tends to be insufficient. On the other hand, if it exceeds 180 minutes, the water absorption performance may possibly be deteriorated in some cases.

(Pressure Reduction)

In the present invention, it is preferable to set the inside of the transverse type continuous stirring apparatus to slightly reduced pressure. "Pressure-reduced state" means barometric pressure lower than atmospheric pressure. In addition, "degree of pressure reduction relative to atmospheric pressure" means the pressure difference with the atmospheric pressure and is denoted as a positive (plus) value in the case where barometric pressure is lower than atmospheric pressure. For example, in the case where atmospheric pressure is standard atmospheric pressure (101.3 kPa), the expression that "degree of pressure reduction is 10 kPa" means that barometric pressure is 91.3 kPa. In this application, "degree of pressure reduction relative to atmospheric pressure" may also be referred to simply as "degree of pressure reduction". In the case where pressure is not reduced, a water absorbent resin powder may possibly flow over the air intake port of the mixing apparatus and it is thus not preferable. Dust (ultrafine particles of the water absorbent resin or inorganic fine particles used if necessary) is removed from the water absorbent resin by slightly reducing the pressure and thus it is also preferable in terms of a decrease in dust.

From the viewpoint of improvement of the effect attributed to pressure reduction, the lower limit of the degree of pressure reduction is preferably higher than 0 kPa, more preferably 0.01 kPa or higher, and still more preferably 0.05 kPa or higher. Excess pressure reduction may possibly remove even a necessary water absorbent resin powder besides dust to the outside of the apparatus and it may possibly result in a decrease in yield. Additionally, from the viewpoints of suppression of leap of a powder in the system and of suppression of excess cost for the exhaust system, the degree of pressure reduction is preferably 10 kPa or lower, more preferably 8 kPa or lower, still more preferably 5 kPa or lower, and particularly preferably 2 kPa or lower. The preferable numeral range of the degree of pressure reduction may be selected arbitrarily between the lower limit and the upper limit.

(Atmosphere)

The atmosphere in the transverse type continuous stirring apparatus may be air, or an inert gas such as nitrogen for prevention of coloration or prevention of combustion, and steam may be added properly. The temperature and the dew point are determined properly, and the atmospheric temperature (defined as the gas temperature in the upper part space of the apparatus) is preferably 30 to 200° C. and more preferably 50 to 150° C. The dew point is preferably 0 to 100° C. and more preferably 10 to 80° C.

(5-3) Cooling Step (a) Cooling Temperature

In the present invention, in order to accomplish the object of the present invention, the water absorbent resin taken out of the heating apparatus after surface-crosslinking is cooled preferably within 1 minute and more preferably within 30 seconds. Consequently, the heating apparatus and the cooling apparatus are preferable to be practically joined to each other. In terms of physical properties and productivity, the temperature (defined as a material temperature) of the water absorbent resin at the time of starting cooling is preferably 150 to 250° C., and the temperature after cooling is preferably 40 to 100° C. The temperature after cooling is more preferably 50 to 90° C. and still more preferably 50 to 80° C.

In the present invention, preferably in the cooling step, the temperature is adjusted to a temperature range overlapped on or conformed with the above temperature of the water absorbent resin before surface-crosslinking and at that time, the inner surface area of the cooling apparatus is controlled within a specified range.

(b) Cooling Apparatus

An apparatus to be used for cooling is not particularly limited as long as it can control the temperature in the inside of the cooling apparatus or the temperature of the water absorbent resin powder by using a refrigerant. Examples thereof include a groove type mixing and cooling apparatus, a rotary cooling apparatus, a disk cooling apparatus, a fluidized bed cooling apparatus, a paddle type cooling apparatus, a vibrating and fluidizing cooling apparatus, and a paddle cooling apparatus using air current in combination and the like.

A mixing apparatus capable of ventilating air current and having a function as a cooling apparatus may be used widely as a cooling apparatus having a rotary shaft and being employed for stirring and cooling, and the direction of the air current such as up and down direction or right and left direction is not particularly limited as long as the apparatus can accomplish the purpose.

Specifically, examples of the cooling apparatus include apparatuses having a horizontal rotary shaft and a container rotating by itself (various kinds of mixing apparatuses such as a horizontal cylindrical type apparatus, an inclined cylindrical type apparatus, a V-formed type apparatus, a double conical type apparatus, a cubic type apparatus, an S-formed type apparatus, and a continuously V-shaped type apparatus), and apparatuses having a horizontal rotary shaft and a fixed container (various kinds of mixing apparatuses such as a ribbon type apparatus, a screw type apparatus, a conical screw type apparatus, a groove stirring type apparatus, a high speed fluidization type apparatus, a rotary disk type apparatus, a Muller type apparatus, a paddle type apparatus, a rotary type apparatus, and a disk type apparatus), which can control the temperature of the cooling apparatus using a refrigerant, and apparatuses for cooling the water absorbent resin powder while fluidizing the powder by using vibration and air current in combination, for example, apparatuses enabled to control the temperature of the cooling apparatus using a refrigerant for a heat transfer tube such as a cooling tube in a continuous vibration type drying and cooling apparatus manufactured by Tamagawa Machinery Co. Ltd., a vibration type drier and cooling apparatus manufactured by Dalton Co., Ltd., a vibration type fluidized bed drying and cooling apparatus manufactured by Tsukishima Kikai Co. Ltd., or the like. The cooling apparatus is preferably a container-fixed type cooling apparatus equipped with rotating stirring blades for stirring the water absorbent resin particles and capable of ventilating air current, and the cooling apparatus is preferable to be used while using a refrigerant. The cooling apparatus as described above is used continuously or in a batch manner, and is preferably used continuously. Herein, it is preferable to carry out the periodic shielding for the inlet of the cooling apparatus (joined to the outlet of the heating apparatus) and further for the outlet of the cooling apparatus.

Among these cooling apparatuses, in terms of improvement of physical properties and stabilization, a transverse type continuous stirring apparatus is preferable. Especially, a (transverse type) continuous stirring apparatus showing the following stirring power index (c) is preferably usable.

That is, as the cooling apparatus and/or heating apparatus in the present invention, it is preferable to use a transverse type continuous stirring apparatus having a charging inlet and a discharge outlet for a water absorbent resin, as well as a stirring means including one or more of rotary shafts equipped with a plurality of stirring disks, and a heating means, and at that time, the preferred conditions for the heating apparatus, such as the stirring power index, the inclined angle (0.1 to 10°, more preferably 0.5 to 5°, and still more preferably 1 to 4° for the transverse type continuous stirring apparatus) the aspect ratio (more preferably 1.5 to 10 and still more preferably 2 to 5), the scraping blades, the average retention time, the rotary shaft, and the stirring disks are preferably applicable to the preferred conditions for the cooling apparatus within a range for keeping the inner surface area ratio or the inner volume ratio.

(c) Stirring Power Index

As the cooling apparatus in the present invention, it is preferable to use a transverse type continuous stirring apparatus having a charging inlet and a discharge outlet for a water absorbent resin, as well as a stirring means including one or more of rotary shafts equipped with a plurality of stirring disks, and a heating means, which is the same as the continuous heating apparatus. The heating means includes a heating means for cooling a high temperature water absorbent resin. The cooling step is carried out preferably in the joined transverse type continuous stirring apparatus (e.g., FIG. 3).

In that case, the cooling is carried out while adjusting the stirring power index to 3 to 15 W·hr/kg. Herein, the stirring power index is defined by the following formula.

(Stirring power index)=((power consumption of apparatus at the time of cooling)−(power consumption at the time of idling)×average retention time)/(treatment amount per unit time×average retention time).

Herein, a water absorbent resin with high physical properties can be continuously and stably obtained even at the time of scale-up to a large scale (particularly, 1 t/hr or more) based on a specified apparatus and specified parameters thereof (stirring power index). The stirring power index can easily be calculated from the power consumption at the time of cooling and the power consumption at the time of idling. If this stirring power index exceeds 15 W·hr/kg, the physical properties (particularly, liquid permeability) are deteriorated and on the other hand, if it is under 3 W·hr/kg, the physical properties (particularly, water absorption against pressure)

are also deteriorated. The stirring power index is more preferably in a range of 4 to 13 W·hr/kg, still more preferably 5 to 11 W·hr/kg, particularly preferably 5 to 10 W·hr/kg, and most preferably 5 to 9 W·hr/kg.

The stirring power index (4 to 13 W·hr/kg, more preferably 5 to 11 W·hr/kg, particularly preferably 5 to 10 W·hr/kg, and most preferably 5 to 9 W·hr/kg) of the heating apparatus described above (also known as heat treatment apparatus, heater) may be the same or different from that of the cooling apparatus; however, in terms of physical properties, the stirring power index of the cooling apparatus (also known as chiller) is preferable to be smaller. The stirring power index of the cooling apparatus is preferably in a range of 0.99 to 0.25 times, more preferably 0.95 to 0.50 times, and particularly preferably 0.90 to 0.55 times as high as that of the heating apparatus.

The stirring power index of the cooling apparatus can be determined properly in accordance with adjustment of the supply amount and discharge amount of the water absorbent resin, the particle size or bulk specific gravity of the water absorbent resin, the size, rotation speed and shape of the apparatus, the composition of the surface treatment agent, and the retention time in the same manner as in the stirring power index of the heating apparatus.

(d) Inner Surface Area Ratio and Inner Volume Ratio of Heating Apparatus and Cooling Apparatus In the heating apparatus and the cooling apparatus, the inner surface area of the cooling apparatus in the cooling step in the present invention is 0.25 to 0.95 times as large as that of the heating apparatus in the surface-crosslinking step. That is, the inner surface area of the cooling apparatus is made smaller than that of the heating apparatus. Herein, the inner surface area is defined as the surface area of a portion with which the water absorbent resin is brought into contact and is the total surface area of the inner surface including the inner wall (side surface) and bottom surface of the apparatus and also the contact surface areas of stirring blades and stirring shafts in the case where the apparatus has such stirring blades and stirring shafts. In the case where the apparatus has stirring blades and stirring shafts, the side surface (inner surface) of the apparatus is defined as the side surfaces up to the most upper parts of the stirring blades and the stirring shafts. In addition, examples of the shape of the inner surface of the apparatus is not limited to a rectangular parallelepiped and include various kinds of shapes such as cylindrical shapes, and their composite shapes, and the inner surface area is defined in accordance with the side surfaces and bottom surfaces thereof. The inner volume is defined by effective volume (volume up to the stirring blades).

Various apparatuses can be employed as an apparatus for adjusting the inner surface area ratio as described above, and in terms of effect, both the heating apparatus and the cooling apparatus are preferably the transverse type continuous stirring apparatus. In that case, the inner surface area ratio may be adjusted to the above range. The inner volume ratio (cooling apparatus/heating apparatus) is also preferably in a range of 0.25 to 0.95 times, more preferably 0.30 to 0.90 times, still more preferably 0.40 to 0.80 times, and particularly preferably 0.50 to 0.75 times. If the inner volume ratio is higher than 0.95 times, the physical properties (e.g., AAP and SFC) tend to be lowered and if it is smaller than 0.25 times, the physical properties tend to be deteriorated, the stability thereof tends to be lowered (an increase in standard deviation) and the water absorbent resin tends to be agglomerated. In the case where apparatuses having similar shapes are used as the heating apparatus and the cooling apparatus, if one of the inner surface area ratio (proportional to the square of the length) and the inner volume ratio (proportional to the cube of the length) is measured, the other can be calculated.

If the inner surface area ratio of the heating apparatus and the cooling apparatus is out of the above range, it is found that it significantly affects the physical properties of the water absorbent resin, particularly the water absorption against pressure and the liquid permeability, and especially the physical properties and the liquid permeability represented by SFC in the case where an ion bonding crosslinking agent is used in combination as the surface-crosslinking agent. The inner surface area ratio (cooling apparatus/heating apparatus) is preferably 0.25 to 0.95 times, more preferably 0.30 to 0.90 times, still more preferably 0.40 to 0.80 times, and particularly preferably 0.50 to 0.75 times. If the inner surface area ratio is higher than 0.95 times, the physical properties (e.g., AAP and SFC) tend to be lowered and if it is smaller than 0.25 times, the physical properties tend to be deteriorated, the stability thereof tends to be lowered (an increase in standard deviation) and the water absorbent resin tends to be agglomerated. The inner volume ratio of both (cooling apparatus/heating apparatus) is also preferably 0.25 to 0.95 times, more preferably 0.30 to 0.90 times, still more preferably 0.40 to 0.80 times, and particularly preferably 0.50 to 0.75 times. If the inner volume ratio is higher than 0.95 times, the physical properties (e.g., AAP and SFC) tend to be lowered and if it is smaller than 0.25 times, the physical properties tend to be deteriorated, the stability thereof tends to be lowered (an increase in standard deviation) and the water absorbent resin tends to be agglomerated.

(e) Condition of Refrigerant Temperature in Stirring and Cooling Treatment

In the present invention, the refrigerant temperature of the cooling apparatus is preferably higher than the dew point of the ambient gas of the cooling apparatus by 10° C. or more and lower than the temperature at the time of discharge of the water absorbent resin particles to be discharged out of the cooling apparatus by 10° C. or lower.

As the cooling apparatus, an apparatus having a jacket in which a refrigerant is circulated on the wall surface is preferable. It is because heat transfer cooling is possible. Other cooling methods may be employed further in combination. The refrigerant temperature is normally −50 to 90° C., preferably 0 to 70° C., and more preferably 10 to 60° C. and in the present invention, it is found that control of the refrigerant temperature within a specified range prevents deterioration of the performance of the water absorbent resin and produces the water absorbent resin more stably and efficiently.

That is, the refrigerant temperature of the cooling apparatus is preferable to be set to the temperature higher than the temperature of a gas introduced into the cooling apparatus, and more preferably to a temperature range higher than the dew point of the gas by 10° C. or more and lower than the temperature at the time of discharge of the water absorbent resin powder to be discharged out of the cooling apparatus by 10° C. or lower. The refrigerant temperature of the cooling apparatus is preferably set to a temperature range higher than the dew point of the gas introduced into the cooling apparatus by 15° C. or more and lower than the temperature at the time of discharge of the water absorbent resin powder to be discharged by 15° C. or lower.

In the case where the difference of the refrigerant temperature and the dew point of the gas to be introduced into the cooling apparatus is less than 10° C., dew is formed in the cooling apparatus and it may possibly cause firm adhesion of agglomerates of the water absorbent resin particles to the inner surface of the apparatus, breakage of the surface-crosslinking structure due to absorption of water in the reformed water absorbent resin and deterioration of the performance. In the case where the difference of the refrigerant temperature and the temperature at the time of discharge of the water absorbent resin powder to be discharged is less than 10° C., it may also result in worsening of the cooling efficiency (heat transfer efficiency) and deterioration of the water absorbent resin (coloration and performance deterioration) due to the heat. If the capacity of the apparatus is increased in order to compensate the worsened cooling efficiency, the performance of the water absorbent resin may be caused due to mechanical damage. In addition, the cost of the apparatus is increased.

The refrigerant to be used is not particularly limited; however, hot water is preferable. Particularly, hot water at an inlet temperature of 30° C. or higher is preferable. The hot water is more preferably at 35° C. or higher, still more preferably at 40° C. or higher, and particularly preferably at 45° C. or higher. The upper limit of the hot water temperature is preferably 55° C. and more preferably 50° C. In the case where the hot water is not at 30° C. or higher or in the case where a refrigerant other than water is used, the water absorbent resin may possibly be deteriorated in its physical properties or may be agglomerated in some cases.

In order to control the refrigerant temperature, it is preferable to carry out a step of measuring the discharge temperature of the water absorbent resin powder and a step of measuring the dew point of a gas to be introduced into the cooling treatment apparatus. If the refrigerant temperature or the refrigerant flow rate is controlled based on the results, the refrigerant temperature can be managed. Regarding the control of the refrigerant temperature or the refrigerant flow rate, computer-programmed management is preferable.

(f) Gas Flow

It is preferable that ventilating current (gas flow) is generated in the space of the cooling apparatus. In the case where there is no forcible ventilation from the outside or to the outside, not only the moisture absorption fluidity (powder fluidity after moisture absorption; anti-blocking property) of the water absorbent resin after cooling is deteriorated, but also the physical properties such as water absorption against pressure are not stabilized. As the gas flow, air, inert gas (nitrogen gas or the like), or a mixture thereof may be used and the gas flow may be at reduced pressure, pressurized, or normal pressure. A blowing mechanism or a pressure reducing mechanism may be installed in the outside of the cooling apparatus so as to ventilate the gas flow at normally −50 to 100° C., preferably 0 to 50° C., and more preferably 10 to 40° C. to the cooling apparatus. In some cooling apparatuses, there is a type of cooling apparatus which has rotary stirring shafts (mixing blades); however, their rotation is not for generating gas flow. In the present invention, the blowing mechanism or the pressure reducing mechanism may be employed for ventilating gas flow. When stirring and cooling are carried out, examples of a method of ventilating gas flow include, but are not limited to, a method of opening an intake port in one side of a cooling apparatus and suctioning gas (decreasing pressure) in another port or a method of opening one gas discharge port of a cooling apparatus and blowing gas (pressurizing) from another port etc.

(5-4) Others (a) Number of Surface Treatment Apparatuses

In terms of improvement of the stirring power index and physical properties, the polymerization step may be carried out preferably by continuous belt polymerization or continuous kneader polymerization and a plurality of surface treatment steps are preferably carried out in parallel for the polymerization step.

In the production method of the present invention, in terms of improvement of physical properties and stabilization, the surface-crosslinking step is carried out in 2 or more lines for 1 line of the polymerization step. The 1 line in the present invention means one system in which steps proceed from a raw material (monomer) until when a polymer gel, a water absorbent resin (including a recovered fine powder product), a particulate water absorbent agent and a final product are obtained. In the case where the system is branched into two, it is referred to as "2 lines". In other words, "2 or more lines" means a mode in which two or more apparatuses are arranged in parallel and operated simultaneously or alternately in a single step.

In the present invention, in the case where the respective steps are carried out in 2 or more lines, the upper limit for each step is about 10 lines, especially preferably 2 to 4 lines, still more preferably 2 to 3 lines, and particularly preferably 2 lines. The physical properties of a water absorbent resin to be obtained are improved by adjusting the number of the lines within the above range. From a viewpoint that in the case where the number of lines (divisions) is large, no dividing effect is caused, and the operation becomes complicated, and also it is not economical in terms of the cost, it is particularly preferable to simultaneously operate 2 lines, that is, 2 or more of the same apparatuses (particularly two apparatuses) in parallel.

In the present invention, the polymer gel or the water absorbent resin, which is a dried product of the polymer gel, is divided into 2 or more lines in the steps after the drying step, and the ratio of amounts divided may be determined for every step without any particular limitation. For example, in the case of dividing into 2 lines, the ratio is preferably 4:6 to 6:4, more preferably 4.5:5.5 to 5.5:4.5, still more preferably 4.8:5.2 to 5.2:4.8, and most preferably 5:5. Even in the case of dividing into 3 or more lines, it is preferable that the ratio of the maximum amount and the minimum amount of n divided portions is within the above range. The dividing operation may be carried out in a continuous manner or in a batch manner and the ratio of amounts divided is defined in accordance with the average amounts for a prescribed time.

In the present invention, the number of lines in the surface-crosslinking step is not particularly limited and the number thereof may be selected arbitrarily; however, in consideration of the construction cost and running cost of a plant etc., 1 line or 2 lines are preferable and 2 lines are particularly preferable. That is, in terms of physical properties, it is most preferable that the surface-crosslinking step and preferably further the crushing step and the classification step all have 2 or more lines (the upper limit is within the above range) for 1 line of the polymerization step.

In addition, in the case where a plurality of apparatuses are installed in parallel in place of one apparatus in the present invention, the apparatuses in parallel may properly be miniaturized. Even if the treatment capacity of the apparatus is miniaturized into ½, the cost of the apparatus is not lowered to a half, however, in the present invention, installation of specified apparatuses in parallel improves the physical properties of an absorbent agent to be obtained and decreases the ratio of the product out of the specification and it is thus found that it consequently results in a decrease in cost.

US Patent Application Publication No. 2008/0227932 discloses a technique of carrying out "polymerization in 2 lines" and the latter half in one line; Patent Document 30 (US Patent Application Publication No. 2007/149760) discloses a technique of "joining in series" of a stirring and drying apparatus and a heating apparatus for surface-crosslinking; and WO 2009/001954 discloses a technique of "joining in series" of belt polymerization apparatuses. In contrast, in the present invention, the physical properties are improved and stabilization is accomplished more than before by "arranging (substantially the same) apparatuses in parallel" in the specified step after completion of the polymerization step for one polymerization apparatus.

(Dividing Means)

In order to carry out surface-crosslinking in 2 or more lines in the present invention, a dividing step is included, and a dividing step of a particulate a hydrous gel-like or a particulate water absorbent resin, which is a dried product of the gel, is preferably included, and a dividing step of a particulate water absorbent resin is more preferably included.

A dividing method to be employed may be, for example, the following means (a-1) to (a-3) for the particulate water absorbent resin after drying.

(a-1) A method for dividing the particulate water absorbent resin after storage in a hopper. Preferably, a quantitative feeder for a powder is used. As the quantitative feeder, a cycle feeder or a screw feeder is used suitably.

(a-2) A method for dividing the particulate water absorbent resin during the time of pneumatic transportation to a plurality of hoppers.

(a-3) A method for dividing the particulate water absorbent resin at the time of dropping (e.g., free fall). In this case, a riffle divider, a 3-way divider, or the like having hills and dams are used for the dividing. Additionally, a JIS sample reducing and dividing apparatus (riffle divider) has a structure partitioned into a large number of small chambers in which a fed sample is distributed alternately to two directions.

A dividing method to be employed for the polymer gel after polymerization may be, for example, the following means (a-4) to (a-6) or the combination thereof, and the polymer gel is supplied to the drying step in parallel.

(a-4) A method for dividing the particulate hydrous gel obtained by a kneader or a meat chopper at the time of dropping (e.g., free fall). For the dividing, a riffle divider, a 3-way divider, or the like having hills and dams are used in the outlet of the kneader or the meat chopper.

(a-5) A method for dividing the particulate hydrous gel by a quantitative feeder.

(a-6) A method for cutting a sheet-like gel obtained by belt polymerization.

Among them, it is preferable that at least the particulate water absorbent resin after drying is divided and in order for that, the polymerization gel or the particulate dried product is divided.

A preferable value of the dividing ratio of the particulate water absorbent resin and the polymerization gel to be divided in the mode is as described above.

Among them, the means (a-1) to (a-3) are preferably employed and the means (a-1) is more preferably employed in terms of the quantitative supplying property.

(b) Hopper

In terms of the surface-crosslinking property in the present invention, a hopper is preferable to be used before and after the surface-crosslinking. The hopper to be employed is more preferably a hopper with an inverse truncated pyramidal shape, an inverse circular truncated conical shape, a shape formed by adding a square pillar with the same shape as the maximum diameter part of an inverse truncated pyramid to the pyramid, a shape formed by adding a cylindrical column with the same shape as the maximum diameter part of an inverse circular truncated cone to the cone. The material thereof is not particularly limited; however, a hopper made of stainless steel is preferable to be employed and the surface roughness thereof is within the above range preferably. A preferable hopper and the shape thereof are exemplified in PCT/JP 2009/54903 and such a hopper is recommended.

(c) Transportation of Water Absorbent Resin Before and After Surface-Crosslinking Various kinds of methods may be employed as a method of transporting the water absorbent resin before and after surface-crosslinking, and preferably pneumatic transportation is employed. From a viewpoint that the excellent physical properties of the water absorbent resin particles and/or water absorbent resin powder can be maintained stably and the obstruction phenomenon can be suppressed, dried air is preferable to be employed as primary air and secondary air used based on the necessity (additional air for pneumatic transportation). The dew point of the air is generally $-5°$ C. or lower, preferably $-10°$ C. or lower, more preferably $-12°$ C. or lower, and particularly preferably $-15°$ C. or lower. The range of the dew point is $-100°$ C. or higher, preferably $-70°$ C. or higher, and it is sufficient about $-50°$ C. in consideration of cost. Further, the temperature of the gas is 10 to 40° C. and more preferably about 15 to 35° C. The adjustment of the dew point of compressed air to be used at the time of pneumatic transportation to the above range can suppress a decrease in SFC, especially, at the time of wrapping the water absorbent resin as a product and thus, it is preferable.

Besides the use of the dried gas (air), heated gas (air) may be used. A heating method is not particularly limited and a gas (air) may be directly heated using a heat source or the transportation part or pipe may be heated to indirectly heat a gas (air) flowing therein. The temperature of the heated gas (air) is preferably 20° C. or higher and more preferably 30° C. or higher, and preferably lower than 70° C. and more preferably lower than 50° C.

A method of controlling the dew point, a gas, preferably air, may be dried properly. Specifically, examples thereof include a method using a membrane drier, a method using a cooling and adsorption type drier, a method using a diaphragm drier, or a method using these methods in combination. In the case where an adsorption type drier is used, it may be of thermal regeneration manner, a non-thermal regeneration manner, or a non-regeneration manner.

(6) Other Steps

Besides the above-mentioned steps, as required, a recycling step of the evaporated monomer, a granulating step, a fine powder removing step, a fine powder recycling step, etc. may be added. Further, in order to exhibit the effect of color stabilization over time, prevent gel deterioration, or the like, an additive described below may be used for the monomer or the polymer thereof.

[3] POLYACRYLIC ACID (SALT)-TYPE WATER ABSORBENT RESIN (1) Physical Properties of Polyacrylic Acid (Salt)-Type Water Absorbent Resin In the case the purpose is to use the polyacrylic acid (salt)-type water absorbent resin of the present invention for a sanitary material, particularly a paper diaper, it is preferable to control at least one of the following (a) to (e), further two or more including AAP, and still more three or more by the above-mentioned polymerization and surface-crosslinking. In the case the followings are not satisfied, the water absorbent resin sometimes fails to exhibit sufficient function in form of a high concentration diaper described below. The production method of the present invention is more effective for producing a water absorbent resin attaining the following physical properties and particularly for improving and stabilizing the physical properties (narrowing the standard deviation). That is, among the following physical properties of interest, the production method of the prevent invention is preferably applied to a method for producing a water absorbent resin having a water absorption against pressure (AAP) of 20 g/g or higher for an aqueous 0.9 mass % sodium chloride solution at a pressure of 4.8 kPa, a 0.69 mass % physiological saline flow conductivity (SFC) of 1 ($\times 10^{-7} \cdot cm^3 \cdot s \cdot g^{-1}$) or higher, and a water absorption under no pressure (CRC) of 20 g/g or higher, and more preferably applied to a production method within the following range to improve or stabilize the physical properties.

(a) Water Absorption Against Pressure (AAP)

In order to prevent leakage in a diaper, the water absorption against pressure (AAP) for an aqueous 0.9 mass % sodium chloride solution under a pressure of 1.9 kPa and that of 4.8 kPa is controlled to be preferably 20 g/g or higher, more preferably 22 g/g or higher, and still more preferably 24 g/g or higher as one example of means for accomplishing the surface-crosslinking and the cooling step carried out thereafter. The AAP is more preferable as it is higher; however, in terms of the balance between other physical properties and cost, the upper limit of the AAP is about 40 g/g at 1.9 kPa and about 30 g/g at 4.8 kPa. The AAP is shown as a value at 4.8 kPa unless otherwise specified.

(b) Liquid Permeability (SFC)

In some cases, in order to prevent a leakage from a diaper, the liquid permeability under pressure, which is a flow conductivity SFC (defined in U.S. Pat. No. 5,669,894) to a 0.69 mass % physiological saline flow conductivity (SFC) is controlled to be 1 ($\times 10^{-7} \cdot cm^3 \cdot s \cdot g^{-1}$) or higher, preferably 25 ($\times 10^{-7} \cdot cm^3 \cdot s \cdot g^{-1}$) or higher, more preferably 50 ($\times 10^{-7} \cdot cm^3 \cdot s \cdot g^{-1}$) or higher, still more preferably 70 ($\times 10^{-7} \cdot cm^3 \cdot s \cdot g^{-1}$) or higher, and particularly preferably 100 ($\times 10^{-7} \cdot cm^3 \cdot s \cdot g^{-1}$) or higher as one example of means for accomplishing the surface-crosslinking and the cooling step carried out thereafter.

In order to more effectively improve the liquid permeability, especially to improve SFC to 25 ($\times 10^{-7} \cdot cm^3 \cdot s \cdot g^{-1}$) or higher, the present invention is preferably applied for producing a water absorbent resin with high liquid permeability.

(c) Water Absorption Under no Pressure (CRC)

Water absorption under no pressure (CRC) is controlled to be preferably 10 (g/g) or higher, more preferably 20 (g/g) or higher, still more preferably 25 (g/g) or higher, and particularly preferably 30 (g/g) or higher. The CRC is more preferable as it is higher, and the upper limit is not particularly limited; however, in consideration of balance with other physical properties, it is preferably 50 (g/g) or lower, more preferably 45 (g/g) or lower, and still more preferably 40 (g/g) or lower.

(d) Amount of Water Soluble Components (Dissolve Amount)

The amount of water soluble components is preferably 0 to 35 mass % or lower, more preferably 25 mass % or lower, still more preferably 15 mass % or lower, and particularly preferably 10 mass % or lower.

(e) Residual Monomer

Using the above-mentioned polymerization as one example of achieving means, the amount of the residual monomer is adjusted to be generally 500 ppm by mass or lower, preferably 0 to 400 ppm by mass, more preferably 0 to 300 ppm by mass, and particularly preferably 0 to 200 ppm by mass.

(2) Other Additives

Further, in accordance with the purpose, 0 to 3 mass % and preferably 0 to 1 mass % of an oxidizing agent, an antioxidant, water, a polyvalent metal compound, a water-insoluble inorganic or organic powder such as silica and metal soap, etc. as well as a deodorant, an antibacterial agent, a polymer polyamine, pulp, and thermoplastic fibers, etc. may be added to the water absorbent resin.

(3) Purpose of Use

The purpose of use of the polyacrylic acid (salt)-type water absorbent resin of the present invention is not particularly limited; however, it is preferable to use the water absorbent resin for an absorbing article such as a paper diaper, a sanitary napkin, an incontinence pad, or the like. Particularly, the water absorbent resin exhibits excellent performance in case of being used in a high-consistency diaper (one diaper in which a large amount of the water absorbent resin is used) that conventionally has a problem of malodor and coloring derived from raw materials and particularly in the case of being used in a top layer part of an absorbent body of the absorbing article.

The content (core concentration) of the water absorbent resin in the absorbent body which may contain arbitrarily other absorbing materials (pulp fibers or the like) in the absorbing article is 30 to 100 mass %, preferably 40 to 100 mass %, more preferably 50 to 100 mass %, still more preferably 60 to 100 mass %, particularly preferably 70 to 100 mass %, and most preferably 75 to 95 mass % to exhibit the effect of the present invention. For example, in the case where the water absorbent resin of the present invention is used especially for an upper layer part of an absorbent body in the above concentration, the water absorbent resin is excellent in the dispersion property of an absorbed liquid such as urine or the like owing to the high liquid permeability (liquid permeability against pressure) and therefore, an absorbent product such as paper diaper can efficiently distribute a liquid and improve the amount absorbed by the whole of the absorbent product. Additionally, since the absorbent body keeps highly advanced white color, an absorbent product with sanitary impression can be provided.

EXAMPLES

Hereinafter, the effects of the present invention will be made apparent by way of examples; however, the present invention should not be construed in a limited way based on the description of the examples. In addition, measurement methods for AAP, SFC, and the like in the following description are as described above. The measurement methods for the following physical properties (A) and (B) are also described below. In addition, unless otherwise specified, the crushing step, surface-crosslinking step, and cooling step were carried out in slightly reduced pressure (0.28 to 0.31 kPa).

(A) Presence or Absence of Agglomerates of Discharged Water Absorbent Resin Powder A water absorbent resin powder discharged out of a cooling apparatus was classified by a sieve with 850 μm meshes, and presence or absence of agglomerates with a size of 850 μm or larger was confirmed by eye observation and evaluated.

(B) Adhesion State in Cooling Apparatus

The adhesion state of water absorbent resin particles and/or agglomerates thereof in the cooling apparatus during continuous operation was evaluated by eye observation.

<Evaluation Results>

⊙: No adhesive material at all.

○: Scarce adhesion and even in the case of adhesion, the adhesive materials are removed by self-cleaning.

Δ: Partial adhesion occurred.

x: Many adhesive materials

Production Example 1

Sodium persulfate and L-ascorbic acid were continuously mixed by line mixing with an aqueous partially neutralized acrylic acid sodium salt solution (neutralization ratio: 71 mol %, monomer concentration: 38 mass %) containing 0.05 mol % (relative to monomer) of polyethylene glycol diacrylate (the number of addition moles of ethylene glycol: n=9) as an inner crosslinking agent. In this line mixing, the mixing ratio of the sodium persulfate was adjusted to 0.12 g per one mole of the monomer and the mixing ratio of the L-ascorbic acid was adjusted to 0.005 g per one mole of the monomer. The mixture was continuously supplied to a horizontal steel belt polymerization apparatus and subjected continuously to static aqueous solution polymerization (belt retention time: about 30 minutes, thickness: about 25 mm), the obtained hydrous gel-like crosslinked polymer was pulverized into particulate by a meat chopper, and the resultant was spread thinly on a porous plate of a band drier and dried continuously by hot air blow at 160 to 180° C. for 30 minutes. A block-like dried polymer was obtained at the outlet of the drier. The obtained dried polymer was continuously supplied at 1.1 t/hr to a three-step roll granulator, followed by crushing. The obtained water absorbent resin particles at about 60° C. were classified by a sieving apparatus having a sieving net with a mesh size of 850 µm to obtain water absorbent resin particles (1) (mass average particle diameter: 400 µm) containing about 90 mass % or higher of particles having a particle diameter of 150 to 850 µm.

The obtained water absorbent resin particles (1) had a water absorption rate under no pressure (CRC) of 40 g/g and an amount of water extractables of 11 mass %.

The obtained water absorbent resin particles (1) were further continuously supplied at 1 t/hr to a high speed continuous mixing apparatus (Turbulizer manufactured by Hosokawa Micron Group/1000 rpm) and an aqueous surface treatment agent solution (1) containing 1,4-butanediol/propylene glycol/water at a ratio of 0.38/0.63/3.5 (parts by mass to 100 parts by mass of the water absorbent resin particles (1)) was sprayed in the form of droplets with an average particle diameter of about 200 µm to the water absorbent resin particles (1), followed by mixing to obtain a wet mixture (1).

Next, the obtained mixture (1) was continuously heated at 195° C. for 50 minutes by a paddle type low speed stirring type indirect heat drier (paddle drier) to obtain a water absorbent powder (surface-crosslinked water absorbent resin powder) containing several thousand ppm of remaining polyhydric alcohols.

Production Example 1 was carried out according to the method described in Production Example 1A of Patent Document 41 (U.S. Pat. No. 7,378,453).

Comparative Example 1

A refrigerant (cold water) at 40° C. was allowed to flow in a paddle drier with the same form which was connected further in series, successively from the heat treatment by the paddle drier (manufactured by Nara Machinery Co., Ltd.) in Production Example 1. While the inside of the cooling apparatus was maintaining at a reduced pressure of 100 mm $H_2O$ by allowing lightly suctioning gas current to flow in an upper space of the cooling apparatus, the water absorbent powder was cooled by the cooling apparatus (jacket was at 40° C.). After the cooling, the water absorbent powder was classified by a sieve with 850 µm meshes and the water absorbent resin powder obtained consequently was excellent in the fluidity at the time of moisture absorption, showed the physical properties stabilized with the lapse of time, and contained practically no fine powder (100 µm or smaller), and no agglomeration was observed at the time of production. The evaluation results of CRC, AAP, and SFC are shown in Table 1. In addition, a portion of the water absorbent resin fine particles was removed by gas current at the time of cooling.

Comparative Example 1 was carried out according to the method described in Production Example 1A of Patent Document 41 (U.S. Pat. No. 7,378,453). The dew point of the introduced gas not disclosed in the patent document was adjusted to 17° C.

Example 1

Operations were carried out in the same manner as in Comparative Example 1, except that a paddle drier with an approximately similar figure to that of the heating apparatus (paddle drier) and having an inner surface area 0.7 times as wide as that of the heating apparatus was used as a cooling apparatus. The results are shown in Table 1.

Comparative Example 2

Operations were carried out in the same manner as in Comparative Example 1, except that a paddle drier with an approximately similar figure to that of the heating apparatus (paddle drier) and having an inner surface area 0.2 times as wide as that of the heating apparatus was used as a cooling apparatus, and the results are shown in Table 1.

Comparative Example 3

The water absorbent resin particles (1) obtained in Production Example 1 were continuously supplied at 3.6 kg/hr to a high speed mixing apparatus and a water-based liquid (referred to as a surface treatment agent) containing 1,4-butanediol/propylene glycol/water at a ratio of 0.32/0.5/2.73 parts by mass was added to 100 parts by mass of the water absorbent resin particles by spraying in the high speed mixing apparatus. The wet mixture to which the surface treatment agent was added by spraying was continuously supplied to a paddle type low speed stirring type indirect heat drier (CD drier CD-80 Model, manufactured by KURIMOTO LTD., hereinafter referred to as heating apparatus) with the total inner volume of 4.6 L and in which the height of the outlet bank was adjusted in such a manner that the average retention time was adjusted to about 40 minutes. The heat medium temperature was 212° C.

The water absorbent powder, which was surface-crosslinked by heating, was continuously supplied to the same CD drier CD-80 Model as above installed in series and in which the height of the outlet bank was adjusted in such a manner that the average retention time was adjusted to about 30 minutes, followed by stirring and cooling. When the temperature was measured at the position (site) with ⅓ length of the whole length of the cooling apparatus from the outlet side, it was 65° C. and water was added by spraying under the conditions of an amount of water supplied of 0.6 g/minute and an air pressure of 0.02 MPa from the upper side of the position by a two-fluid nozzle manufactured by Spraying Systems Japan (Air atomizing nozzle SUF 1, flat pattern). The water absorbent resin to which water was added by spraying did not form bulky agglomerates (dumpling) in the apparatus and discharged out of the outlet in a smoothly flowing state.

Example 2

Operations were carried out in the same manner as in Comparative Example 3, except that the cooling apparatus (CD drier) was changed to a cooling apparatus having an inner surface area 0.7 times as large as that of the heating apparatus (CD drier) (reduced-size version with an approximately similar figure to that of the CD drier), and the results are shown in Table 2.

Comparative Example 4

Operations were carried out in the same manner as in Comparative Example 3, except that the cooling apparatus (CD drier) was changed to a cooling apparatus having an inner surface area 0.2 times as large as that of the heating apparatus (CD drier) (reduced-size version with an approximately similar figure to that of the CD drier), and the results are shown in Table 2.

Comparative Example 5

A water absorbent resin crosslinked with a covalent bonding crosslinking agent and an ion bonding crosslinking agent (aluminum sulfate) was obtained by changing the water added by spraying at 0.6 g/minute (1 mass % to the water absorbent resin particles (1)) to an aqueous solution of 50% aluminum sulfate hexadeca hydrate in Example 1. Herein, as shown in Table 2, the ion bonding crosslinking agent can be supposed to contribute to improvement of the liquid permeability.

Example 3

Operations were carried out in the same manner as in Comparative Example 5, except that the cooling apparatus (paddle drier) was changed to a cooling apparatus having an inner surface area 0.7 times as large as that of the heating apparatus (paddle drier) (reduced-size version with an approximately similar figure to that of the paddle drier), and the results are shown in Table 2.

Example 4

In Example 1, a periodically shielding apparatus (rotary valve) was installed in the inlet and outlet of the cooling apparatus (paddle drier). The results are shown in Table 1. The volume per one rotation of the rotary valve was 0.02 [$m^3$/lev (one rotation)] and the rotation speed was 25 rpm. The shielding interval was 0.04 minutes (defined as the reciprocal number of the rotation speed, and thus it was 1/25=0.04 minutes because of 25 rpm).

Example 5

In Example 2, a periodically shielding apparatus (rotary valve) which was the same as that in Example 4 was installed in the inlet and outlet of the cooling apparatus. The results are shown in Table 2.

Example 6

Operations were carried out in the same manner as in Example 1, except that the surface-crosslinking was carried out in 2 lines in parallel (500 kg/hr×2 lines). The results are shown in Table 1.

TABLE 1

|  |  | Comparative Example 1 (note 1) | Example 1 | Comparative Example 2 | Example 4 | Example 6 |
|---|---|---|---|---|---|---|
| Heating apparatus |  | paddle drier | paddle drier | paddle drier | paddle drier | paddle drier |
| Feed amount | [kg/hr] | 1000 | 1000 | 1000 | 1000 | 500 × 2 |
| Rotary valve |  | none | none | none | use | none |
| Additive agent |  | none | none | none | none | none |
| Cooling appratus |  | paddle drier | paddle drier | paddle drier | paddle drier | paddle drier |
| Inner surface area ratio |  | 1 | 0.7 | 0.2 | 0.7 | 0.7 |
| Dew point | [° C.] | 17 | 17 | 17 | 17 | 17 |
| Refrigerant temperature | [° C.] | 40 | 40 | 40 | 40 | 40 |
| Water absorbent resin powder |  |  |  |  |  |  |
| CRC | [g/g] | 30.0 | 30.1 | 29.0 | 30.3 | 30.1 |
| AAP | [g/g] | 25.0 | 25.5 | 24.6 | 25.6 | 25.5 |
| SFC | [×$10^{-7}$ · $cm^3$ · s · $g^{-1}$] | 20 | 25 | 24 | 27 | 26 |
| Standard deviation |  |  |  |  |  |  |
| CRC |  |  |  |  | 0.27 |  |
| AAP |  |  |  |  | 0.21 |  |
| SFC |  |  |  |  | 0.51 |  |

(Note 1):
correspond to Example 1A of Patent Document 41 (Non-disclused dew pointwas adjusted to 17° C.)

TABLE 2

|  |  | Comparative Example 3 (note 2) | Example 2 | Comparative Example 4 | Example 5 | Comparative Example 5 | Example 3 |
|---|---|---|---|---|---|---|---|
| Heating apparatus |  | CD drier | CD drier | CD drier | CD drier | CD drier | CD drier |
| Feed amount | [kg/hr] | 3.6 | 3.6 | 3.6 | 3.6 | 3.6 | 3.6 |
| Rotary valve |  | none | none | none | use | none | none |
| Additive agent |  | water 1 mass % | water 1 mass % | water 1 mass % | water 1 mass % | Al sulfate aqueous solution | Al sulfate aqueous solution |
| Cooling appratus |  | CD drier | CD drier | CD drier | CD drier | CD drier | CD drier |
| Inner surface area ratio |  | 1 | 0.7 | 0.2 | 0.7 | 1 | 0.7 |

TABLE 2-continued

|  |  | Comparative Example 3 (note 2) | Example 2 | Comparative Example 4 | Example 5 | Comparative Example 5 | Example 3 |
|---|---|---|---|---|---|---|---|
| Dew point | [° C.] | 17 | 17 | 17 | 17 | 17 | 17 |
| Refrigerant temperature | [° C.] | 40 | 40 | 40 | 40 | 40 | 40 |
| Water absorbent resin powder |  |  |  |  |  |  |  |
| CRC | [g/g] | 28.0 | 28.0 | 27.0 | 28.2 | 27.5 | 27.6 |
| AAP | [g/g] | 25.0 | 25.5 | 24.4 | 25.6 | 24.1 | 24.5 |
| SFC | [×10$^{-7}$ · cm$^3$ · s · g$^{-1}$] | 25 | 30 | 30 | 32 | 42 | 53 |
| Standard deviation |  |  |  |  |  |  |  |
| CRC |  |  |  |  | 0.58 |  |  |
| AAP |  |  |  |  | 0.62 |  |  |
| SFC |  |  |  |  | 1.73 |  |  |

(Note 2):
correspond to Example 1 of Patent Document 41 (Non-disclosed dew point was adjusted to 17° C.)

Example 7

In Example 1, the dew point of air to be introduced was adjusted to 40° C. Partial agglomeration of the water absorbent resin was observed and adhesion was observed in a portion of the inner part. It was found that the dew point (preferably difference from the refrigerant temperature by 10° C. or more) in Example 1 was preferable.

Example 8

In Example 1, the refrigerant was adjusted to 10° C. Partial agglomeration of the water absorbent resin was observed and adhesion was observed in a portion of the inner part. It was found that the refrigerant temperature (preferably hot water at 30° C. or higher) in Example 1 was preferable.

Example 9

The water absorbent resin powder obtained in Example 2 was pneumatically transported by allowing compressed air (dew point −15° C. and temperature 35° C.) to flow in a pipe with a surface roughness (Rz) of 200 nm in the inner surface and wrapped. The SFC after the pneumatic transportation was 29.5 and the SFC decrease ratio was 1.7%.

Example 10

Pneumatic transportation which was the same as that in Example 9 was carried out, except that compressed air with a dew point of 20° C. was used. The SFC after the pneumatic transportation was 28.5 and the SFC decrease ratio was 5.0%.

(Conclusion)

As shown in Tables 1 and 2, the water absorption against pressure and liquid permeability, and particularly liquid permeability were improved by controlling the capacity (inner surface area) of the cooling apparatus. The physical properties were improved and stabilized by combination use of the periodically shielding apparatus, parallel execution (division) of surface-crosslinking and cooling, and control of the dew point of a gas to be introduced into the cooling apparatus.

From the results of in Example 9 and Example 10, it was found that pneumatic transportation using compressed air with specified dew point was preferable.

Production Example 2

A continuous production apparatus for a polyacrylic acid (salt)-type water absorbent resin was used which was obtained by connecting respective apparatuses for a polymerization step (static polymerization on a belt), a gel shredding step (pulverization step), a drying step, a crushing step, a classification step, and a transportation step between the respective steps and which could carry out the respective steps continuously. The production capacity of this continuous production apparatus was about 1500 kg per an hour. Water absorbent resin particles were continuously produced by using this continuous production apparatus.

First, an aqueous acrylic acid sodium salt solution partially neutralized at 75 mol % was prepared as an aqueous monomer solution (2). The aqueous monomer solution (2) contained 0.055 mol % of polyethylene glycol diacrylate (average n number=9) as an inner crosslinking agent relative to the total mole number. The concentration of the monomer (partially neutralized acrylic acid sodium salt) in the aqueous monomer solution (2) was 40 mass %. The obtained aqueous monomer solution (2) was continuously fed onto a belt by a constant rate pump. Nitrogen gas was continuously blown in the middle of the pipe used for the feeding and the oxygen concentration dissolved in the aqueous monomer solution (2) was adjusted to 0.5 mg/L or lower. In addition, the above-mentioned "average n number" means the average number of degree of methylene chain polymerization in the polyethylene glycol chain.

Next, 0.10 g/mol of sodium persulfate and 0.005 g/mol of L-ascorbic acid were continuously mixed by line mixing with the aqueous monomer solution (2). In this line mixing, the mixing ratio of the sodium persulfate was adjusted to 0.12 g per one mole of the monomer and the mixing ratio of the L-ascorbic acid was adjusted to 0.005 g per one mole of the monomer. The continuously mixed material obtained by line mixing was supplied in a thickness of about 30 mm to a flat plane steel belt having banks in both ends and subjected continuously to static aqueous solution polymerization for about 30 minutes to obtain a hydrous gel-like crosslinked polymer (2). The hydrous gel-like crosslinked polymer (2) was finely shredded into about 2 mm by a meat chopper with a hole diameter of 7 mm, spread on a movable porous plate of a continuous ventilating band drier in such a manner that the thickness thereof was adjusted to 50 mm, and dried at 185° C. for 30 minutes to obtain a dried polymer. Herein, the time taken from the outlet of the polymerization apparatus to the inlet of the drier was within 1 minute. The entire amount of the dried polymer was continuously supplied to a three-step roll mill, followed by crushing. The roll gaps of the three-step roll mill were 1.0 mm/0.55 mm/0.42 mm in this order from the upper side. After the crushing, the crushed polymer was classified by a sieving apparatus having metal sieving nets with 850 μm meshes and 150 μm meshes to obtain water absorbent resin particles (2) containing about 98 mass % of particles having a particle diameter of 150 to 850 μm. The CRC of the water absorbent resin particles (2) was 35 g/g and the bulk specific gravity thereof was 0.6 g/cm³.

Example 11

A water absorbent resin powder (11) was produced by using a continuous production apparatus involving a surface treatment step (wetting and mixing step, heating step, and cooling step), a particle regulation step, and a transportation step joining the respective steps, successively from the continuous production apparatus used in Production Example 2. That is, the classification step of Production Example 2 and the surface treatment step were joined by the transportation step.

The water absorbent resin particles (2) were pneumatically transported to a temporarily storing hopper by pneumatic transportation (temperature 35° C. and dew point −15° C.) from the classifying apparatus and continuously supplied at 1.5 t/hr via a constant rate feeder by a high speed continuous mixing apparatus (Turbulizer; 1000 rpm; e.g., FIG. 4) and at the same time a surface treatment agent solution (11) was mixed by spraying (wetting and mixing step). The surface treatment agent solution (11) was a mixed solution containing 1,4-butanediol, propylene glycol, and pure water. The surface treatment agent solution (11) was mixed with the water absorbent resin particles (2) at a ratio of 0.3 parts by mass of 1,4-butanediol, 0.5 parts by mass of propylene glycol, and 2.7 parts by mass of pure water relative to 100 parts by mass of the water absorbent resin particles (2) to give a mixture (11), a wet powder.

The obtained mixture (11) was then surface-treated by a transverse type continuous stirring apparatus (11) having a downward inclined angle of 1°, an aspect ratio of 2.2, a paddle rotation speed of 13 rpm, two rotary shafts, and stirring disks having scraping blades, and a surface roughness (Rz) of the inner surface of 500 nm (heat treatment step). At that time, the inside of the apparatus (11) was suctioned by a suctioning gas discharge apparatus having a bag filter, and the inside pressure of the apparatus was reduced to 1 kPa. A rotary valve (periodically shielding apparatus) was installed in the inlet (joining part with the mixing apparatus) and outlet (joining part with the cooling apparatus) of the apparatus (11). According to a previous test, the position of a discharge bank which gave an average retention time of about 45 minutes and an average filling ratio of 75% was measured, and the discharge bank was set at the position as measured. A heating source used for the surface treatment was pressurized steam at 2.5 MPa, and the temperature of the mixture (11) in the apparatus was measured by a thermometer installed near the discharge part of the transverse type continuous stirring apparatus (11), and the steam flow rate was controlled to carry out the heating in such a manner that the temperature was adjusted to 200° C. The total surface area of the stirring disks and the stirring shafts was 24.4 m² and the mass surface area ratio calculated from the total surface area (heat transfer surface area) and the treatment amount was 61.5 kg/m²/hr. The stirring power at the time of the surface treatment was 27.8 kW, the stirring power in idling was 13.5 kW, the average retention time was 45 minutes, and the stirring power index was 9.5 W·hr/kg.

Using a compact transverse type continuous stirring apparatus (cooling apparatus) having a similar shape to and an inner surface area of 0.80 times as wide as the transverse type continuous stirring apparatus (11), a heating apparatus, the hot water flow rate at 40° C. was adjusted, so that the water absorbent resin was forcibly cooled to 60° C. (cooling step). The stirring power index was 7.4 W·hr/kg.

The water absorbent resin discharged at 60° C. was classified by a sieving apparatus to separate the substance under 850 μm, and the substance on 850 μm (substance not passed through 850 μm) was again crushed and mixed with the substance under 850 μm to give a water absorbent resin powder (11), as a particle size-regulated product which was the total amount of the substance under 850 μm.

The obtained water absorbent resin powder (11) had a CRC of 30.7 (g/g) of, an SFC of 29.9 ($\times 10^{-7}$·cm³·s·g⁻¹) of, an AAP of 25.2 (g/g) of, and a bulk specific gravity of 0.68 g/cm³. The standard deviation of each physical property value was CRC: 0.16, SFC: 0.48, and AAP: 0.13. Additionally, these physical property values were average values of the measurement carried out by sampling (5 points) every an hour until 5 hours were passed from the starting of the operation.

Comparative Example 6

Operations were carried out in the same manner as in Example 11, except that a transverse type continuous stirring apparatus (cooling apparatus) with the same size as that of the transverse type continuous stirring apparatus (11) as a heating apparatus was used in place of the compact transverse type continuous stirring apparatus having a similar shape and an inner surface area of 0.80 times. The SFC and AAP were decreased to 28.1 ($\times 10^{-7}$·cm³·s·g⁻¹) and 24.7 (g/g), respectively, by making the inner surface area of the cooling apparatus 1.0 time as large as the inner surface area of the heating apparatus.

Comparative Example 7

Operations were carried out in the same manner as in Example 11, except that a compact transverse type continuous stirring apparatus (cooling apparatus) having an approximately similar shape and an inner surface area of 0.1 times was used in place of the compact transverse type continuous stirring apparatus having a similar shape and an inner surface area of 0.80 times. The surface-crosslinking reaction was not stopped sufficiently and agglomeration of a portion of the water absorbent resin was observed and the physical properties were not stabilized since the inner surface area of the cooling apparatus was made to be 0.1 times as large as the inner surface area of the heating apparatus to be used in the heat surface-crosslinking step.

(Comparison with Conventional Techniques)

As compared with the techniques in Patent Documents 1 to 41, the physical properties of a water absorbent resin are improved and stabilized (a decrease in standard deviation). As an improvement technique for the cooling step, Patent Document 41 or the like is known; however, such an improvement technique in apparatuses does not indicate the present application, and it corresponds to comparative examples of the present application.

INDUSTRIAL APPLICABILITY

A water absorbent resin with high physical properties, particularly, high liquid permeability is provided by continuous production in a huge scale (e.g., 1 t/hr or more).

EXPLANATION OF REFERENCE NUMERALS

10: Driving apparatus
20: Transverse type drum

30: Raw material supply port
40: Heat medium inlet
40': Heat medium inlet
45': Heat medium outlet
50: Water absorbent resin discharge port
70: Rotary shaft
80: Stirring disk
80a: Stirring disk
80b: Stirring disk
81: Carrier gas introduction port
85: Gas discharge port
90: Scraping blade
90a: Scraping blade
90b: Scraping blade
100: Stirring apparatus (stirring means)

The invention claimed is:

1. A method for producing a polyacrylic acid (salt) water absorbent resin, comprising steps of:
preparing an aqueous monomer solution of acrylic acid (salt),
polymerizing the aqueous monomer solution,
finely shredding a hydrous gel-like crosslinked polymer during or after polymerization,
drying the obtained particulate hydrous gel-like crosslinked polymer,
crushing the dried polymer,
classifying the dried polymer,
heating and surface-crosslinking the dried polymer after the classification, and
cooling after the surface-crosslinking, wherein
the inner surface area of a cooling apparatus to be used in the cooling step is 0.25 to 0.95 times as large as the inner surface area of a heating apparatus to be used in the heating and surface-crosslinking step.

2. A method for producing a polyacrylic acid water absorbent resin, comprising steps of:
preparing an aqueous monomer solution of acrylic acid (salt),
polymerizing the aqueous monomer solution,
finely shredding a hydrous gel-like crosslinked polymer during or after polymerization,
drying the obtained particulate hydrous gel-like crosslinked polymer,
crushing the dried polymer,
classifying the dried polymer,
heating and surface-crosslinking the dried polymer after the classification, and
cooling after the surface-crosslinking, wherein
the inner volume of a cooling apparatus to be used in the cooling step is 0.25 to 0.95 times as large as the inner volume of a heating apparatus to be used in the heating and surface-crosslinking step.

3. The production method according to claim 1 or 2, wherein the cooling apparatus and/or the heating apparatus is a transverse continuous stirring apparatus having a charging inlet and a discharge outlet for the water absorbent resin, as well as a stifling means including one or more of rotary shafts equipped with a plurality of stirring disks and a heating means.

4. The production method according to claim 1 or 2, wherein a refrigerant in the cooling apparatus in the cooling step is heated to temperature equal to or higher than the dew point of a gas in the cooling apparatus.

5. The production method according to claim 1 or 2, wherein the refrigerant temperature of the cooling apparatus is higher than the dew point of the gas in the cooling apparatus by 10° C. or more and lower than the temperature at the time of discharge of the water absorbent resin particles to be discharged out of the cooling apparatus by 10° C. or lower.

6. The production method according to claim 1 or 2, wherein a refrigerant in the cooling apparatus is hot water at 30° C. or higher.

7. The production method according to claim 3, wherein the cooling apparatus is the transverse continuous stirring apparatus and the apparatus has a stirring power index of 3 to 11 W·hr/kg.

8. The production method according to claim 3, wherein each of the cooling apparatus and the heating apparatus is the transverse continuous stifling apparatus and the stirring power index of the cooling apparatus is 0.25 to 0.95 times as high as that of the heating apparatus.

9. The production method according to claim 1 or 2, further comprising steps of measuring the temperature of the water absorbent resin in the heating and surface-crosslinking step and/or the cooling step and controlling the refrigerant temperature or the flow rate.

10. The production method according to claim 1 or 2, wherein the inner surface of the cooling apparatus and/or the heating apparatus is of stainless steel with a surface roughness of 800 nm or lower.

11. The production method according to claim 1 or 2, wherein the water absorbent resin particles before the surface-crosslinking step and/or after the cooling step are pneumatically transported at a dew point of −5° C. to −100° C.

12. The production method according to claim 1 or 2, wherein the surface-crosslinking step has 2 or more lines for 1 line in the polymerization step.

13. The production method according to claim 1 or 2, wherein the classification step, surface-crosslinking step, and cooling step are carried out in reduced pressure.

14. The production method according to claim 1 or 2, wherein a covalent bonding crosslinking agent and an ion bonding crosslinking agent are used in combination as the surface-crosslinking agent in the heating and surface-crosslinking step.

15. The production method according to claim 1 or 2, wherein the cooling apparatus is a continuous cooling apparatus having a periodically shielded inlet.

16. The production method according to claim 1 or 2, wherein the water absorbent resin before the surface-crosslinking and after the cooling is at a temperature within a range of 40 to 100° C.

* * * * *